US007193125B2

(12) United States Patent
Moore et al.

(10) Patent No.: US 7,193,125 B2
(45) Date of Patent: Mar. 20, 2007

(54) SCREENING SYSTEMS AND METHODS FOR IDENTIFYING MODULATORS OF XENOBIOTIC METABOLISM

(75) Inventors: David D. Moore, Bellaire, TX (US); Ping Wei, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 316 days.

(21) Appl. No.: 10/219,590

(22) Filed: Aug. 15, 2002

(65) Prior Publication Data

US 2003/0009774 A1 Jan. 9, 2003

Related U.S. Application Data

(63) Continuation of application No. 09/666,250, filed on Sep. 21, 2000, now abandoned.

(51) Int. Cl.
*G01N 33/00* (2006.01)

(52) U.S. Cl. .............................................. 800/3; 800/8

(58) Field of Classification Search .................. 800/18, 800/3, 8; 435/325, 320.1
See application file for complete search history.

(56) References Cited

U.S. PATENT DOCUMENTS

| | | | | |
|---|---|---|---|---|
| 5,710,017 | A | 1/1998 | Moore et al. | |
| 6,579,686 | B2 * | 6/2003 | Collins et al. | 435/7.8 |
| 6,693,226 | B1 | 2/2004 | McNeish | |
| 6,921,845 | B1 | 7/2005 | Amson et al. | |
| 6,987,211 | B1 | 1/2006 | Soreq | |
| 2002/0152479 | A1 * | 10/2002 | Lehmann et al. | 800/3 |

FOREIGN PATENT DOCUMENTS

| | | |
|---|---|---|
| WO | WO-99/15555 A1 | 4/1999 |
| WO | WO-00/47735 A2 | 8/2000 |
| WO | WO-01/51045 A2 | 7/2001 |

OTHER PUBLICATIONS

Cameron E.R. (1997) Recent Adavnces in Transgenic Technology. Molecular Biotechnology. 7:253-265.*

Bowie et al. (1990) Deciphering the Message in Protein Sequences: Tolerance to Amino Acid Substitutions. Science. 247:1306-1310.*

Ngo et al. (1994) The Protein Folding Problem and Tertiary Structure Predicticnj, Merz er (ed.), pp. 437&492-495.*

Houdebine. (2000) Transgenic animal bioreactors. Transgenic Research. 9:305-320.*

Kolb et al. (1999) Insertion of a foriegn gene into the beta-casein locus by Cre-mediated site-specific recombination. Gene 227:21-31.*

Lariviere et al. (2000) Transgenic Studies of Pain and Analgesia:Mutation or Background Genotype. J. of Pharm and Exp. Therap. 297:467-473.*

Leiter et al. (2002) Mice with targeted gene disruptions or gene insertions for diabetes research:problems, pitfalls, and potential solutions. Diabetologia 45:296-308.*

Thiron et al. (2006) Human Gene Therapy 17:193-205.*

Burk et al. (2005) Biol. Chem. 386:503-513.*

Sigmund, C., (2000) Arterioscler. Thromb. Vasc. Biol., p. 1425-1429.*

Baes et al., "A New Orphan Member of the Nuclear Hormone Receptor Superfamily that interacts with a Subset of Retinoic Acid Response Elements," Molecular And Cellular Biology 14(3):1544-1552 (1994).

Bornheim, "Effect of Cytochrome P450 Inducers on Cocaine-mediated Hepatoxicity," Toxicology And Applied Pharmacology 150:158-165 (1998).

Blumberg et al., "SXR, a Novel Steroid and Xenobiotic-Sensing Nuclear Receptor," Genes Dev., 12:3195-3205 (1998).

Carthew et al., "The Quantitative Distinction of Hyperplastic in Hepatomegaly Induced in the Rat Liver by Phenobarbital," Toxicological Science 44:46-51 (1998).

Choi et al., "Differential Transactivation by Two Isoforms of the Orphan Nuclear Hormone Receptor CAR," The Journal of Biological Chemistry, 272:23565-23571 (1997).

Code et al., "Human Cytochrome P4502B6: Interindividual Hepatic Expression, Substrate Specificity, and Role in Procarcinogen Activation," Drug Metabolism And Disposition 25(8):985-993 (1997).

Cunningham, "Role of Increased DNA Replication in the Carcinogenic Risk of Nonmutagenic Chemical Carcinogens," Mutation Research 365:59-69 (1996).

Heubel et al., "Differences between Induction Effects of 1,4-bis[2-(3,5-dichloropyridyloxy)]Benzene and Phenobarbitone," Biochemical Pharmacology 38:1293-1300 (1989).

Honkakoski et al., "Characterization of Phenobarbital-inducible Mouse Cyp2b10 Gene Transcription in Primary Hepatocytes," The Journal of Biological Chemistry 271(16):9746-9753 (1996).

Honkakoski et al., "The Nuclear Orphan Receptor CAR-Retinoid X Receptor Heterodimer Activates the Phenobarbital-Responsive Enhancer Module of the CYP2B Gene," Molecular And Cellular Biology 18(10):5652-5658 (1998).

Jones et al., "The Pregnane X Receptor: A Promiscuous Xenobiotic Receptor that has Diverged during Evolution," olecular Endocrinology 14(1):27-39 (2000).

Kliewer et al., "An Orphan Nuclear Receptor Activated by Pregnanes Defines a Novel Steroid Signaling Pathway," Cell 92:73-82 (1998).

Lehmann et al., "The Human Orphan Nuclear Receptor PXR Is Activated by Compounds that Regulate CYP3A4 Gene Expression and Cause Drug Interactions," J. Clin. Invest. 102(5):1016-1023 (1998).

(Continued)

*Primary Examiner*—Deborah Crouch
*Assistant Examiner*—Louis D Lieto
(74) *Attorney, Agent, or Firm*—Fulbright & Jaworski LLP

(57) ABSTRACT

The present invention provides mice having reduced CAR receptor activity and mice expressing a human CAR receptor. These mice are useful in screening methods to identify compounds that modulate CAR receptor activity, compounds likely to have CAR-mediated toxicity, and analogs of these compounds with less potential toxicity.

10 Claims, 4 Drawing Sheets

OTHER PUBLICATIONS

Moore et al., "Orphan Nuclear Receptors Constitutive Androstane Receptor and Pregnane X Receptor Share Xenobiotic and Steroid Ligands," The Journal Of Biological Chemistry 275(20):15122-15127 (2000).
Pellinen et al., "Regenerative changes in Hepatic Morphology and Enhanced Expression of CYP2B10 and CYP3A During Daily Administration of Cocaine," Hepatology 23(3):515-523 (1996).
Poland et al., "1,4-Bis[2-(3,5-Dichloropyridyloxy)]Benzene, a Potent Phenobarbital-like Inducer of Microsomal Monooxygenase Activity," Molecular Pharmacology 18:571-580 (1980).
Robinson et al., "Genetic Expression of Aryl Hydrocarbon Hydroxlase Induction. Presence or Absence of Association with Zoxazolamine, Diphenylhydantoin, and Hexobarbital Metabolism," Molecular Pharmacology 10:484-493 (1974).
Selim et al., "Hepatotoxicity of Psychotropic Drugs," Hepatology 29(5):1347-1351 (1999).
Shimada et al., "Interindividual Variations in Human Liver Cytochrome P-450 Enzymes Involved in the Oxidation of Drugs, Carcinogens and Toxic Chemicals: Studies with Liver Microsomes of 30 Japanese and 30 Caucasians," The Journal Of Pharmacology And Experimental Therapeutics 270(1):414-423 (1994).
Sueyoshi et al., "The Repressed Nuclear Receptor CAR Responds to Phenobarbital in Activating the Human CYP2B6 Gene," The Journal Of Biological Chemistry 274(10):6043-6046 (1999).
Traber et al., "Differential Regulation of Cytochrome P-450 Genes along Rat Intestinal Crypt-villus Axis," Am. J. Physiol. 263:G215-223 (1992).
Tzameli et al., "The Xenobiotic Compound 1,4-Bis[2-(3,5-Dichloropyridyloxy)]Benzene Is an Agonist Ligand for the Nuclear Receptor CAR," Molecular And Cellular Biology 20(9):2951-2958 (2000).
Waxman, "P450 Gene Induction by Structurally Diverse Xenochemicals: Central Role of Nuclear Receptors CAR, PXR, and PPAR," Archives of Biochemistry And Biophysics 369(1):11-23 (1999).
Zhang, Jun, et al.; Modulation of Acetaminophen-induced Hepatotoxicity by the Xenobiotic Receptor CAR; Science, vol. 298, pp. 422-424, Oct. 11, 2002.
Huang, Wendong, et al.: Induction of bilirubin clearance by the constitutive androstane receptor (CAR); PNAS 100(7):4156-4161, Apr. 1, 2003.
Baes et al., "A New Orphan Member of the Nuclear Hormone Receptor Superfamily That Interacts with a Subset of Retinoic Acid Response Elements," *Mol. Cell. Biol.*, 14(3): 1544-1552, 1994.
Garcia-Vallve et al., "Nuclear Receptors, Nuclear-Receptor Factors, and Nuclear-Receptor-like Orphans Form a Large Paralog Cluster in *Homo sapiens," Mol. Biol. Evol.*, 15(6): 665-682, 1998.
Hardouin et al., "Mouse models for human disease," *Clin. Genet.*, 57: 237-244, 2000.
Hayashi et al., "Liver enriched transcription factors and differentiation of hepatocellular carcinoma," *J. Clin. Pathol: Mol. Pathol.*, 52: 19-24, 1999.
Kumar et al., "The structure of the nuclear hormone receptors," *Steroids*, 64: 310-319, 1999.
Moore et al., "Orphan Nuclear Receptors Constitutive Androstane Receptor and Pregnane X Receptor Share Xenobiotic and Steroid Ligands," *J. Biol. Chem.*, 275(20): 15122-15127, 2000.
Tenbaum et al., "Nuclear Receptors: Structure, Function, and Involvement in Disease," *Int. J. Biochem. Cell Biol.*, 29(12): 1325-1341, 1997.
Tzameli et al., "The Xenobiotic Compound 1,4-Bis[2-(3,5-Dichloropyridyloxy)]Benzene Is an Agonist Ligand for the Nuclear Receptor CAR," *Mol. Cell. Biol.*, 20(9):2951-2958, 2000.
Wei et al., "The nuclear receptor CAR mediates specific xenobiotic induction of drug metabolism," *Nature*, 407: 920-923, 2000.
West et al., "Mouse Genetics/Genomics: An Effective Approach for Drug Target Discovery and Validation," *Med. Res. Rev.*, 20(3): 216-230, 2000.
Oliver, J.D. et al. Receptor-mediated hepatocarcinogenesis: role of hepatocyte proliferation and apoptosis. Pharmacology & Toxicology 2002, vol. 91, pp. 1-7, see the entire document.
Xie W. et al. Reciprocal activation of xenobiotic response genes by nuclear receptors SXR/PXR and CAR. Genes & Development 2000, vol. 14, pp. 3014-3023, see the entire document.
Robertson, G.R. et al. Transgenic mouse models of human CYP3A4 gene regulation. Molecular Pharmacology 2003, vol. 64, No. 1, pp. 42-50, see the entire document.
Xie, W. et al. Humanized xenobiotic response in mice expressing nuclear receptor SXR. Nature Jul. 27, 2000, vol. 406, pp. 435-439, see the entire document.
Xie, W. et al. Control of steroid heme, and carcinogen metabolism by nuclear pregnane X receptor and constitutive androstane receptor. Proceedings of the National Academy of Sciences, USA, Apr. 1, 2003, vol. 100, No. 7, pp. 4150-4155, see the entire document.
Wei, P. et al. The nuclear receptor CAR mediates specific xenobiotic induction of drug metabolism. Nature Oct. 19, 2000, vol. 407, pp. 920-923, see the entire document.
Waxman, David J.; Minireview—P450 Gene Induction by Structurally Diverse Xenochemicals: Central Role of Nuclear Receptors *CAR, PXR,* and *PPAR*; Archives of Biochemistry and Biophysics, 369(1):11-23, 1999.

* cited by examiner

Figure 1A
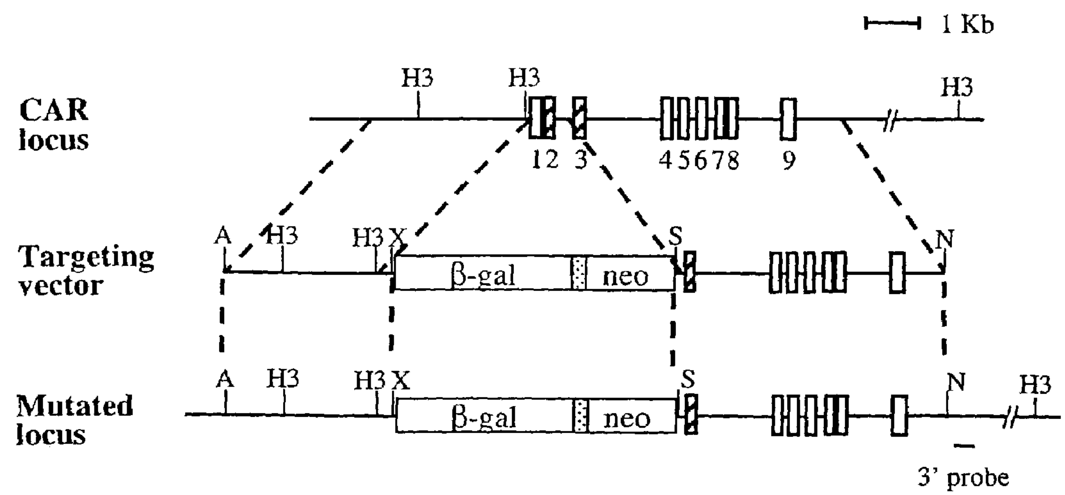
Figure 1B
Figure 1C
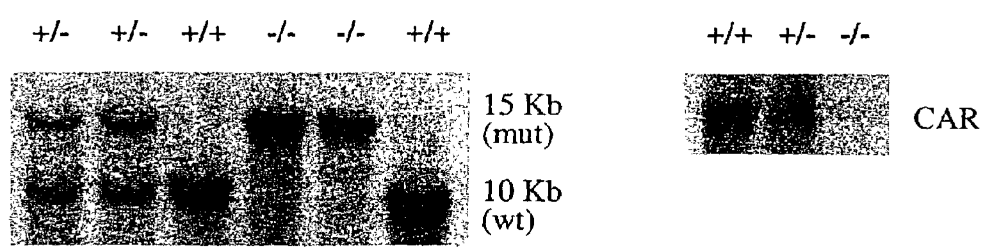

SCREENING SYSTEMS AND METHODS FOR IDENTIFYING MODULATORS OF XENOBIOTIC METABOLISM

CROSS-REFERENCE TO RELATED APPLICATION

This application is a continuation of U.S. utility application Ser. No. 09/666,250, filed Sep. 21, 2000 now abandoned.

STATEMENT AS TO FEDERALLY SPONSORED RESEARCH

This invention was made with government support under NIH grant NIDDK RO1 DK46546. The government therefore has certain rights in the invention.

BACKGROUND OF THE INVENTION

In general, the invention involves screening methods for identifying modulators of metabolism of any of a wide range of foreign compounds, collectively termed xenobiotics.

A number of cytochrome P450 (CYP) enzymes able to metabolize diverse substrates serve as a primary defense against potentially deleterious effects of xenobiotic compounds. Induction of the expression of individual CYP genes in response to particular xenobiotics is a central component of this metabolic mechanism. One of the best characterized of these responses is the induction of specific CYP genes by a diverse group of agents known as "phenobarbital-like" inducers. Exposure of animals to any of a chemically diverse series of compounds exemplified by phenobarbital (PB) results in a potent activation of expression of a specific subset of CYP enzymes and other proteins associated with xenobiotic metabolism. In the mouse, these PB-like inducers increase expression of CYP2B10 and several other genes. The pesticide contaminant 1,4-bis[2-(3,5-dichloropyridyloxy)]benzene, referred to as TCPOBOP, is generally considered to be the most potent of this group of inducers.

Xenobiotics, such as therapeutic drugs, insecticides, polycyclic hydrocarbons, and some natural products, are often metabolized via oxidation reactions catalyzed by CYP enzymes. These reactions add hydrophilic groups to xenobiotics, allowing the body to rid itself of these noxious or simply insoluble materials. For example, oxidation of polycyclic aromatics produces epoxides, which are very reactive electrophilic groups. Usually these epoxides are rapidly hydrolyzed into hydroxyl groups which are then coupled to other groups, producing compounds water-soluble enough to be excreted. Unfortunately, the intermediate epoxides may also be released into the cell as highly reactive electrophiles, possibly reacting with negatively charged groups in DNA and causing changes in the DNA sequence. Reactive oxygen species generated during metabolism of cocaine by CYP enzymes in humans has been associated with mutagenesis and chromosome breakage.

CYP-mediated metabolism may also result in other undesired effects, such as the rapid degradation of a therapeutically active compound, lowering its half-life in vivo. Alternatively, CYP enzymes may convert a prodrug into an active drug at a faster than desired rate resulting in a toxic concentration of the active drug in vivo. Additionally, the activation of CYP enzymes by the administration of a therapeutically active compound or exposure to another foreign compound may result in faster metabolism of a second therapeutically active compound, reducing its effectiveness or increasing its toxicity.

Because of the potentially deleterious effects of compounds that activate CYP enzymes, improved methods are needed to determine which compounds activate CYP-mediated metabolism and, thus, might cause side-effects if administered to humans. These compounds may thereby be eliminated from drug development or chemically modified to generate related compounds with less ability to activate CYP enzymes.

SUMMARY OF THE INVENTION

The present invention provides screening systems and methods that facilitate the identification of compounds that activate or inhibit a CAR receptor. Such CAR receptor-activating compounds are potentially toxic when administered to a mammal alone or in combination with other compounds, and are therefore preferably excluded from candidate drugs or drug development programs. Similarly, compounds that inhibit a CAR receptor may be administered to a mammal to decrease the CAR-mediated metabolism of a therapeutically active compound, potentially decreasing side-effects and re-establishing the therapeutic half-life of the compound in vivo. Such a decrease of metabolic activity may also be useful to decrease production of toxic products from appropriate precursor compounds.

Accordingly, in a first aspect, the invention features a transgenic mouse expressing a human CAR receptor. In a related aspect, the invention features a mouse having a mutation that reduces CAR receptor activity.

The animals of the present invention may be used to determine whether a compound modulates the activity of a CAR receptor. In addition, methods are provided to determine whether the metabolism of a compound is regulated by modulation of the activity of a CAR receptor.

Accordingly, the invention also features a screening method for determining whether a compound activates a CAR receptor. This method involves administering a compound to a transgenic mouse expressing a human CAR receptor and measuring induction of a CAR target gene. The compound is determined to activate the CAR receptor if the compound mediates induction of the CAR target gene. In one preferred embodiment, a CAR receptor inverse agonist is also administered to the mouse expressing a human CAR receptor. Preferably, the CAR receptor inverse agonist is clotrimazole.

In another aspect, the invention features a screening method for determining whether a compound inhibits a CAR receptor. This method involves administering the compound to a transgenic mouse expressing a human CAR receptor and measuring expression of a CAR target gene in the presence and absence of the compound. The compound is determined to inhibit the CAR receptor if the compound decreases the expression of the CAR target gene. In one preferred embodiment, a CAR receptor agonist is also administered to the mouse expressing the human CAR receptor. Preferably, the CAR receptor agonist is a functional CAR receptor agonist that is specific for human CAR, and the agonist is administered after the compound is administered to the mouse.

In yet another aspect, the invention features a screening method for determining whether a compound modulates the activity of a CAR receptor. This method involves administering the compound to a transgenic mouse expressing a human CAR receptor and measuring a physiological effect mediated by the administration of the compound. The compound is determined to modulate the activity of the CAR receptor if the magnitude of the physiological effect in the mouse expressing the human receptor differs from that in a mouse having a mutation that reduces CAR receptor activity. In preferred embodiments, the physiological effect is assayed by measuring the toxicity or activity mediated by the administration of the compound or by measuring the half-life of the compound. In other preferred embodiments, the toxicity or activity is mediated by a metabolite of the compound. Preferably, the difference between the magnitude of the physiological effect in the mouse expressing the human CAR receptor as compared to a mouse having reduced CAR receptor activity is at least 2, 5, 10, or 20-fold. In other preferred embodiments, the magnitude of the physiological effect in a mouse having reduced CAR activity is at least 10, 25, 50, or 75% smaller or larger than the magnitude of the effect in the mouse expressing the human CAR receptor.

In still another aspect, the invention features a screening method for determining whether the metabolism of a compound is regulated by modulation of the activity of a CAR receptor. This method involves administering the compound to a transgenic mouse expressing a human CAR receptor and measuring the rate of metabolism of the compound. The metabolism of the compound is determined to be regulated by modulation of the activity of the CAR receptor if the rate of metabolism is faster in the mouse expressing the human receptor than in a mouse having reduced CAR receptor activity. Preferably, the rate of metabolism is at least 2, 5, 10, or 20-fold faster in the mouse expressing the human CAR receptor than in the mouse having reduced CAR receptor activity. In preferred embodiments, the rate of metabolism is determined by measuring the toxicity or activity mediated by the administration of the compound, measuring the half-life of the compound, or measuring the serum level of a liver enzyme. Preferably, these measurements are performed at more than 1, 3, or 5 time points after administration of the compound.

In another aspect, the invention provides a screening method for determining whether the metabolism of a first compound is modulated by a second compound. This method involves administering the first compound in the presence and absence of the second compound to a transgenic mouse expressing a human CAR receptor. A physiological effect that is mediated by the administration of the first compound is measured in the presence and absence of the second compound. The second compound is determined to modulate the metabolism of the first compound if the second compound effects a change in the physiological effect mediated by the administration of the first compound. In preferred embodiments, the physiological effect is assayed by measuring the toxicity or activity mediated by the administration of the first compound or measuring the half-life of the first compound. In various preferred embodiments, the toxicity or activity is mediated by a metabolite of the first compound. In still another preferred embodiment, the physiological effect is assayed by measuring the half-life of the first compound in the presence and absence of the second compound. The second compound is determined to activate the metabolism of the first compound if the second compound decreases the half-life, or the second compound is determined to inhibit the metabolism of the first compound if the second compound increases the half-life.

Similar methods for determining whether a compound modulates the activity of a CAR receptor or the metabolism of another compound may also be performed using a mouse having a mutation that reduces CAR receptor activity. For example, the invention features a screening method for determining whether a compound activates a CAR receptor. This method involves administering a compound to a mouse having a mutation that reduces CAR receptor activity and measuring induction of a CAR target gene. The compound is determined to activate the CAR receptor if the induction is smaller in the mouse having reduced CAR receptor activity than in a mouse having wild-type CAR receptor activity. In a preferred embodiment, a CAR receptor inverse agonist to is also administered to the mouse having reduced CAR receptor activity. Preferably, the inverse agonist is androstanol.

In another aspect, the invention features a screening method for determining whether a compound inhibits a CAR receptor. This method involves administering the compound to a mouse having a mutation that reduces CAR receptor activity and measuring expression of a CAR target gene in the presence and absence of the compound. The compound is determined to inhibit the CAR receptor if the decrease in expression effected by the compound is smaller in the mouse having reduced CAR receptor activity than in a mouse having wild-type CAR receptor activity. In one preferred embodiment, a CAR receptor agonist is also administered to the mouse having reduced CAR receptor activity. Preferably, the CAR receptor agonist is TCPOBOP, and the TCPOBOP is administered after the compound.

In still another aspect, the invention features a screening method for determining whether a compound modulates the activity of a CAR receptor. This method involves administering the compound to a mouse having a mutation that reduces CAR receptor activity and measuring a physiological effect mediated by the administration of the compound. The compound is determined to modulate the activity of the CAR receptor if the magnitude of the physiological effect in the mouse having reduced CAR receptor activity differs from that in a mouse having wild-type CAR receptor activity. Preferably, the difference between the magnitude of the physiological effect in the mouse having reduced CAR receptor as compared to a mouse having wild-type CAR receptor activity is at least 2, 5, 10, or 20-fold. In other preferred embodiments, the magnitude of the physiological effect in the mouse having reduced CAR activity is at least 10, 25, 50, or 75% smaller or larger than the magnitude of the effect in a mouse having wild-type CAR receptor activity. In yet other preferred embodiments, the physiological effect is assayed by measuring the toxicity or activity mediated by the administration of the compound or measuring the half-life of the compound. In another preferred embodiment, the toxicity or activity is mediated by a metabolite of the compound.

In still another aspect, the invention provides a screening method for determining whether the metabolism of a compound is regulated by modulation of the activity of a CAR receptor. This method involves administering the compound to a mouse having a mutation that reduces CAR receptor activity and measuring the rate of metabolism of the compound. The metabolism of the compound is determined to be regulated by modulation of the activity of the CAR receptor if the rate of metabolism is slower in the mouse having reduced CAR receptor activity than in a mouse having wild-type CAR receptor activity. Preferably, the rate of metabolism is at least 2, 5, 10, or 20-fold slower in the mouse having reduced CAR receptor activity than in a mouse having wild-type CAR receptor activity.

In preferred embodiments, the rate of metabolism is determined by measuring the toxicity or activity mediated by the administration of the compound, measuring the half-life of the compound, or measuring the serum level of a liver enzyme. Preferably, these measurements are performed at more than 1, 3, or 5 time points after administration of the compound.

In yet another aspect, the invention features a screening method for determining whether the metabolism of a first compound is modulated by a second compound. This method involves administering the first compound in the presence and absence of the second compound to a mouse having a mutation that reduces CAR receptor activity. A physiological effect that is mediated by the administration of the first compound is measured in the presence and absence of the second compound. The second compound is determined to modulate the metabolism of the first compound if the change effected by the second compound in the physiological effect mediated by the administration of the first compound is smaller in the mouse having reduced CAR receptor activity than in a mouse having wild-type CAR receptor activity. In preferred embodiments, the physiological effect is assayed by measuring the toxicity or activity mediated by the administration of the first compound or measuring the half-life of the first compound. In various preferred embodiments, the toxicity or activity is mediated by a metabolite of the first compound. In another preferred embodiment, the physiological effect is assayed by measuring the half-life of the first compound in the presence and absence of the second compound. The second compound is determined to activate the metabolism of the first compound if the decrease in the half-life effected by the second compound is smaller in the mouse having reduced CAR receptor activity than in a mouse having wild-type CAR receptor activity, or the second compound is determined to inhibit the metabolism of the first compound if the increase in the half-life effected by the second compound is smaller in the mouse having reduced CAR receptor activity than in a mouse having wild-type CAR receptor activity.

In preferred embodiments of various aspects of the invention, the mouse having a mutation that reduces CAR receptor activity is a transgenic animal. Preferably, the mutation that reduces CAR receptor activity substantially eliminates CAR receptor activity. In yet other preferred embodiments, the mouse having a mutation that reduces CAR receptor activity and the mouse having wild-type CAR receptor activity have the same genotype except for a mutation in the CAR receptor gene, promoter, or regulatory sequence. In still other preferred embodiments, the mouse having wild-type CAR receptor activity is a transgenic mouse expressing a human CAR receptor. Preferably, the mouse expressing a human CAR receptor does not express a substantially active murine CAR receptor or does not express any murine CAR receptor.

Preferred CAR target genes are murine CYP2B10 (SEQ ID NO: 11, Accession No. NM_009998) and a transgene containing human CYP2B6 (SEQ ID NO: 12, GenBank Accession No. AC023172). Other possible CAR target genes include, but are not limited to, other CYP enzymes or other enzymes involved in xenobiotic metabolism. CAR target genes may also include a CAR responsive promoter operably-linked to a reporter gene, such as human growth hormone, secreted alkaline phosphatase, chloramphenicol acetyl transferase, luciferase, green fluorescent protein, CYP2B6, or any other reporter gene (see, for example, Ausubel et al., Current Protocols in Molecular Biology, Chapter 9, John Wiley & Sons, New York, 2000). Examples of appropriate promoters include native CYP promoters, such as the CYP2B10 promoter (Gen Bank Accession No. U48732; Honkakoski et al., J. Biol. Chem. 271, 9746–9753, 1996) containing the previously described phenobarbital response element (Honkakoski et al., Mol. Cell. Biol. 18:5652–5658, 1998) or the CYP2B6 promoter (GenBank Accession No. AC023172), or synthetic promoter constructs in which DNA binding sites for CAR/RXR heterodimers are operably-linked to functional basal promoters (Tzameli et al., Mol. Cell. Biol. 20: 2951–2958, 2000).

In other preferred embodiments, at least one of the compounds tested in the screening methods of the invention is a member of a library of as few as 2 or 5 compounds to as many as 10, 20, 50, or more compounds, all of which are simultaneously administered to the mouse. Preferred routes of administration of the compounds include oral, intramuscular, intravenous, parenteral, intraarticular, intraperitoneal, subcutaneous, or any other suitable route. Preferably, a compound that activates a CAR receptor or a compound whose metabolism is regulated by modulation of the activity of a CAR receptor is eliminated from drug development. If a first compound activates the metabolism of the second compound, then the first compound, the second compound, or both compounds are preferably eliminated from drug development. It is also contemplated that other animal models, such as a rat or other rodent having reduced CAR receptor activity or expressing a human CAR receptor, could be used in any of the various aspects of the invention.

By “CAR receptor activity” is meant CAR-mediated induction of a gene, denoted a “CAR target gene,” or a transgene operably-linked to a CAR responsive promoter. The level of induction of the CAR target gene or transgene may be determined using standard assays for measuring the level of encoded mRNA or protein (see for example, Ausubel et al., Current Protocols in Molecular Biology, John Wiley & Sons, New York, 2000). Alternatively, an enzymatic activity of a CAR target gene, such as the 7-pentoxyresorufin O-dealkylase activity of the CYP2B10 CAR target gene, may be measured (Pellinen et al. Hepatology 23:515–23, 1996). Examples of CAR target genes include CYP2B10 and a CYP2B6 transgene; examples of CAR responsive promoters include the CYP2B10 and CYP2B6 promoters and promoters operably-linked to DNA binding sites for CAR/RXR heterodimers. Alternatively, an increase in CAR receptor activity can be assayed by determining an increase in liver mass relative to total body mass, an increase in release of a liver enzyme such as alanine aminotransferase into the serum, or an increase in DNA synthesis in the liver, using the assays described herein. CAR-mediated induction may be measured in response to a number of xenobiotic compounds, including TCPOBOP.

By “mutation” is meant an alteration in the nucleic acid sequence such that the amino acid sequence encoded by the nucleic acid sequence has at least one amino acid alteration as compared to the naturally-occurring sequence. The mutation may, without limitation, be an insertion, deletion, frameshift mutation, or missense mutation. Alternatively, the mutation may alter the sequence of a CAR receptor promoter, transcriptional regulatory sequence, or translational regulatory sequence such that a smaller amount of CAR mRNA or protein is expressed. Preferably, the mutation results in at least a 25, 35, 50, 70, 80, 90, 95, 99, or 100% reduction in the activity of the encoded CAR receptor compared to the activity of a naturally-occurring CAR receptor. In another preferred embodiment, the level of induction of a CAR target gene in response to a xenobiotic administered to a mouse having a mutation in a CAR receptor is less that 10, 5, or 2-fold times the corresponding level of induction in a CAR null mouse that does not express CAR mRNA or protein.

By "transgenic" is meant any cell or organism which includes a DNA sequence which is inserted by artifice into a cell and becomes part of the genome of the organism which develops from that cell. As used herein, the transgenic organism is generally a transgenic non-human mammal, preferably, a rodent such as a mouse.

By "substantially eliminates CAR receptor activity" is meant reduces the CAR receptor activity by 25, 35, 50, 70, 80, 90, 95, 99, or 100% compared to the activity of a naturally-occurring CAR receptor. In another preferred embodiment, the level of residual CAR receptor activity is no greater than 10, 5, or 2 times the corresponding level of CAR receptor activity in a CAR null mouse that does not express CAR mRNA or protein.

By "a substantially active murine CAR receptor" is meant having at least 30, 60, 80, 90, 95, or 100% of the CAR receptor activity of the naturally-occurring murine CAR receptor encoded by GenBank Accession No. 2267575 in a normal murine host (Choi et al., J. Biol. Chem. 272:23565–23571, 1997) (SEQ ID NO: 1).

By "a human CAR receptor" is meant a protein that has an amino acid sequence at least 75, 80, 90, 95, 99, or 100% identical to the amino acid sequence of the naturally-occurring human CAR receptor, encoded by GenBank Accession No. 458541 (Baes et al., Mol. Cell. Bio. 14:1544–1551, 1994) (SEQ ID NO: 2), and that has at least 50, 75, 80, 90, 95, or 100% of the CAR receptor activity of a naturally-occurring human CAR receptor assayed under identical conditions. It is also contemplated that the expressed human CAR receptor may be a fragment having an amino acid sequence at least 75, 80, 90, 95, 99, or 100% identical to the corresponding region of a naturally-occurring human CAR receptor and having at least 60, 80, 90, 95, or 100% of the CAR receptor activity of a naturally-occurring human CAR receptor. In addition, a human CAR receptor is inhibited by clotrimazole, an inverse agonist of human, but not murine, CAR (Moore et al., J Biol Chem. 275:15122–15127, 2000).

By "activation of a CAR receptor" is meant an increase in the rate of the CAR-mediated induction of a CAR target gene, or a transgene operably-linked to a CAR responsive promoter. Preferably, the increased induction of the CAR target gene or transgene in a mouse results in a 2, 5, 10, or 20-fold increased level of the encoded mRNA or protein, increased enzymatic activity of the CAR target gene, increased relative liver mass, increased release of a liver enzyme such as alanine aminotransferase into the serum, or increased DNA synthesis in the liver, as measured using the assays described herein. In another preferred embodiment, the increased induction is 2, 5, 10, or 20-fold greater in a mouse having wild-type CAR receptor activity than in a mouse having a mutation that reduces CAR receptor activity.

In one preferred embodiment, the candidate activator of a CAR receptor and a CAR receptor inverse agonist are administered to a mouse having a mutation that reduces CAR receptor activity or a mouse expressing a human CAR receptor. The level of induction of a CAR target gene is measured in the presence and absence of the candidate activator to determine whether the candidate activator effects an increase in the level of induction of the CAR target gene. The administration of the CAR receptor inverse agonist may decrease the initial level of induction of the CAR target gene and thus facilitate the detection of a increase in the induction mediated by the candidate activator.

By "inhibit a CAR receptor" is meant decrease the rate of induction of a CAR target gene or transgene operably-linked to a promoter of a CAR target gene. Preferably, the decreased induction of the CAR target gene or transgene in a mouse results in a 2, 5, 10, or 20-fold decreased level of the encoded mRNA, protein, enzymatic activity, relative liver mass, release of a liver enzyme into the serum, or DNA synthesis in the liver, as determined using the assays described herein. In another preferred embodiment, the decrease in the level of induction is 2, 5, 10, or 20-fold greater in a mouse having wild-type CAR receptor activity than in a mouse having a mutation that reduces CAR receptor activity.

In one preferred embodiment, the candidate inhibitor of a CAR receptor and a CAR receptor agonist are administered to a mouse having a mutation that reduces CAR receptor activity or a mouse expressing a human CAR receptor. The level of induction of a CAR target gene is measured in the presence and absence of the candidate inhibitor to determine whether the candidate inhibitor effects a decrease in the level of induction of the CAR target gene. The administration of the CAR receptor agonist may increase the initial level of induction of the CAR target gene and thus facilitate the detection of a decrease in the induction mediated by the candidate inhibitor.

By "having wild-type CAR receptor activity" is meant having a substantially identical activity to that of a naturally-occurring murine or human CAR receptor. By "substantially identical," as used herein, is meant at least 80, 90, 95, 99, or 100% of the activity of a naturally-occurring CAR receptor. The ability of a CAR receptor to induce a CAR target gene or a transgene operably-linked to a CAR responsive promoter may be routinely measured using assays for the encoded mRNA, protein, or enzymatic activity or assays for relative liver mass, a liver enzyme released into the serum, or DNA synthesis.

By "modulate the metabolism" is meant to increase or decrease the rate of a CYP-catalyzed reaction of a compound, such as the oxidation of the compound. For example, the rate of metabolism of the compound may be measured as the rate of formation of the oxidized product or the formation of a subsequent product generated from the oxidized intermediate. Alternatively, the rate of metabolism may be represented as the half-life or rate of disappearance of the initial compound or as the change in toxicity or activity of the initial compound or a metabolite generated in a CYP-dependent manner from the initial compound. For example, a second compound is said to modulate the metabolism of a first compound if the half-life, toxicity, or activity of the first compound is increased or decreased in the presence of the second compound. Preferably, the change in the half-life, toxicity, or activity of the first compound or a metabolite of the first compound is at least 25, 50, 100, 200, 500, or 1000% of the corresponding half-life, toxicity, or activity in the absence of the second compound. In another preferred embodiment, the change in the half-life, toxicity, or activity is at least 2, 5, 10, or 20-fold greater in a mouse having wild-type CAR receptor activity than in a mouse having a mutation that reduces CAR receptor activity. In various preferred embodiments, a second compound mediates a change of at least 2, 5, 10, or 20-fold in the magnitude of the half-life, activity, or toxicity of a first compound or a metabolite of the first compound, as measured in any of the assays described herein.

The half-life may be measured by determining the amount of the compound present in samples taken from the mouse at various time points; the amount of the compound may be quantified using standard methods such as high-performance liquid chromatography, mass spectrometry, western blot analysis using compound specific antibodies, or any other appropriate method. In preferred embodiments, a reaction required for the toxicity or activity of the first compound or a metabolite of the first compound (such as the reaction of an activated metabolite with DNA, RNA, or protein) is at least 25, 50, 100, 200, 500, or 1000% of the corresponding rate in the absence of the second compound. The toxicity of the first compound or a metabolite of the first compound may also be measured by determining the relative liver mass, amount of a liver enzyme released into the serum, or rate of DNA synthesis in the liver of a mouse. It is also contemplated that the rate of a reaction catalyzed by another enzyme involved in xenobiotic metabolism that is downstream of a CAR receptor may also be increased or decreased. In one preferred embodiment, the second compound modulates the metabolism of the first compound by activating or inhibiting a CAR receptor.

By "activity of a compound" is meant a biological effect mediated by a compound. Examples of possible activities of compounds include binding to other molecules, modulation of a binding interaction between molecules, modulation of the rate of catalysis of an enzyme, induction of physiological or behavioral changes, or any other therapeutically relevant activity of a compound.

By "physiological effect" is meant a toxic effect, an activity, or the modulation of the expression of a CAR target gene mediated by a compound, as described above. For compounds that are metabolized to form a metabolite that has a different level of toxicity or activity as the initial compound, the physiological effect of the compound may also be measured by determining the half-life of the compound.

By "promoter" is meant a minimal sequence sufficient to direct transcription of an operably-linked gene. The promoter may also be operably-linked to 5' regulatory sequences that modulate the transcription of the gene.

The present invention provides a number of advantages. For example, the methods of the present invention may be used to facilitate the identification of analogs of a compound that have reduced or undetectable ability to activate a CAR receptor, and thus are expected to have fewer side-effects or a longer half-life in vivo. In addition, because murine and human CAR receptors have somewhat different substrate specificities, the use of transgenic mice expressing a human CAR receptor in the methods of the present invention may more accurately predict the modulation of CAR receptor toxicity or half-life of a compound when administered to humans. Moreover, the present assays may be easily and rapidly performed.

Other features and advantages of the invention will be apparent from the following detailed description and from the claims.

BRIEF DESCRIPTION OF THE DRAWINGS

FIG. 1A is a schematic illustration of the targeted disruption of the mouse CAR gene. Boxes represent exons. Exons 2 and 3 (hatched boxes) contain the DNA binding domain. Homologous recombination resulted in replacement of Exons 1 and 2 with the β-gal and neo resistance genes. Restriction enzyme sites for Apa I (A), Hind III (H3), Not I (N), Sal I (S), and Xba I (X) are indicated.

FIG. 1B is a picture of a gel showing genotype analysis by Southern blotting. Genomic DNA from tail samples was digested with Hind III and hybridized with the 3' probes. The 10 Kb and 15 Kb bands were generated from wild-type and mutant alleles, respectively.

FIG. 1C is a picture of a gel showing Northern blot analysis. The murine CAR cDNA was used as a probe to determine the level of CAR mRNA expressed in liver of wild-type and CAR+/– or –/– animals.

DETAILED DESCRIPTION

The present screening methods and systems stem from the discovery that mice lacking the nuclear hormone receptor CAR (NR114) gene have decreased metabolism of the classic CYP substrate zoxazolamine and are not able to activate expression of the CYP2B10 gene or produce liver hypertrophic or hyperplastic responses upon treatment with either phenobarbital or the more potent inducer TCPOBOP. In contrast, strong activation and toxicity were seen in wild-type mice. In addition, cocaine treatment in the presence of either inducer resulted in acute hepatotoxicity in wild-type mice, but no detectable toxicity in CAR–/– "knockout" mice. Accordingly, the present invention provides screening methods for comparing the activation of CAR target genes, toxicity, and half-life of compounds after administration to mice with reduced or no CAR receptor activity versus administration to wild-type mice. These methods allow the identification of compounds that activate CAR receptors and are potentially toxic to mammals (e.g., humans), as well as compounds that inhibit CAR receptors and reduce the toxicity or CYP-mediated metabolism of a pharmaceutically active compound administered to a mammal.

CAR Receptor Knockout Mice

To assess the functional role of CAR, we generated two independent mouse lines in which a promoter proximal segment of the CAR gene, including a portion of the DNA binding domain, was replaced by the coding region for β-galactosidase (FIG. 1A). As expected, these β-galactosidase "knockin" animals were unable to express CAR mRNA (FIG. 1C). This loss of CAR expression did not result in any overt phenotype; homozygous CAR−/− animals were born at expected Mendelian frequency, and both male and female −/− animals were fertile.

CAR has previously been reported to be expressed predominantly in the liver. To define the pattern of CAR expression in more detail, β-galactosidase expression was examined in CAR+/− heterozygotes. As expected, the β-galactosidase marker was expressed in liver, and expression was highest near the portal vessels. β-galactosidase expression was also observed in the epithelial cells of the small intestine.

Figure 2A:
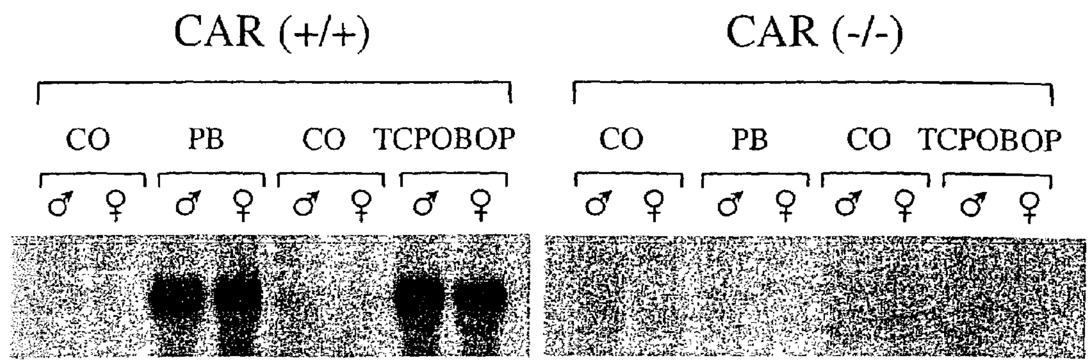
FIG. 2A is a picture of a representative Northern blot of xenobiotic activation of the CYP2B10 gene by CAR in a liver sample. Mice (8–10 weeks old, 3 mice per treatment) were treated with corn oil (CO) for 6 or 24 hours, PB for 24 hours, or TCPOBOP for 6 hours.
Figure 2B:
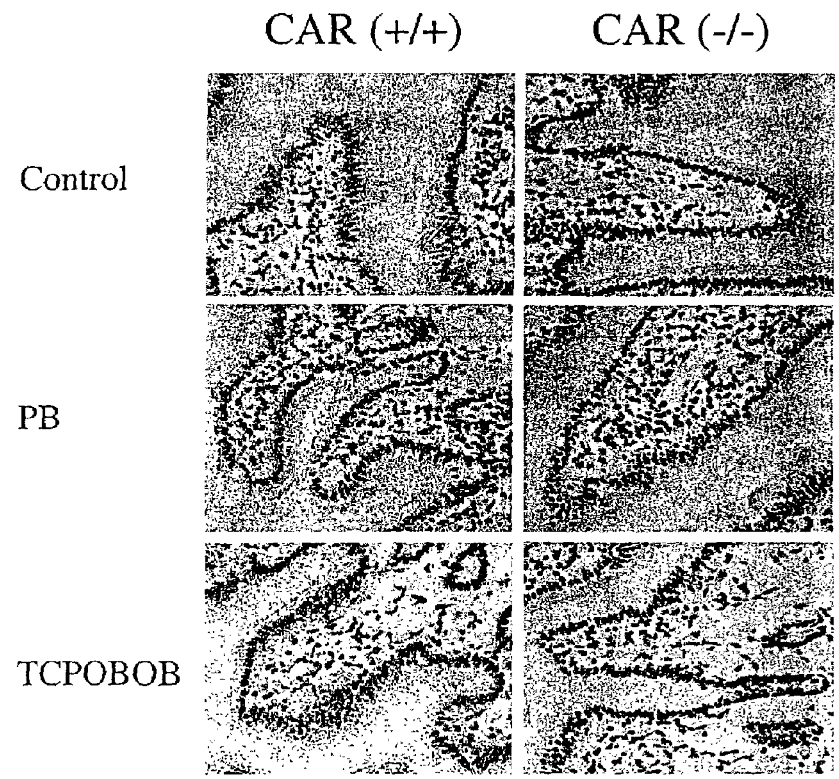
FIG. 2B is a series of photographs of in situ hybridization of a piece of small intestine from mice treated with PB or TCPOBOP for 3 days. The in situ hybridization was performed with an [$^{35}$S]-labeled antisense CYP2B10 riboprobe. The number of grains per cell are not significantly different in the CAR–/– animals, with or without xenobiotic treatment. The number of grains per cell is approximately two-fold higher in the untreated wild-type mice than in the CAR receptor knockout mice, and the number of grains per cell in the xenobiotic-treated wild-type mice is approximately two-fold higher than in the untreated wild-type mice.

To test the role of CAR in the response to PB-like inducers, the effect of treating wild-type and CAR−/− animals with either PB or TCPOBOP was examined. The robust induction of expression of CYP2B10 mRNA in response to either of these two compounds in wild-type male or female animals was completely absent in the knockout animals (FIG. 2A). Similar results were obtained with both independent CAR−/− lines. This requirement for CAR was also demonstrated in the small intestine, using in situ hybridization. As indicated in FIG. 2B, either PB or TCPOBOP also induced CYP2B10 expression in this tissue in wild-type, but not CAR−/− animals. The confinement of specific hybridization to the epithelial cells was consistent with previous results and also with the pattern of CAR expression described above.

Figure 3A:
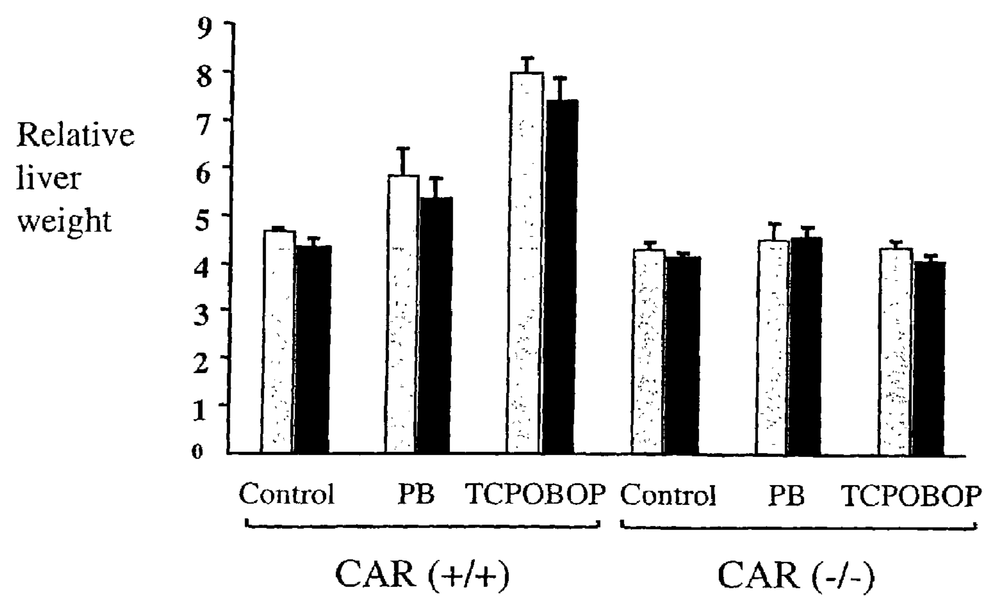
FIG. 3A is a bar graph showing the liver enlargement and hepatocyte proliferation by PB or TCPOBOP. Mice (8–10 weeks old) were treated with PB or TCPOBOP for 3 days, and then both liver mass and body weight were measured. The data is presented as percentage of liver mass relative to total body weight.
Figure 3B:
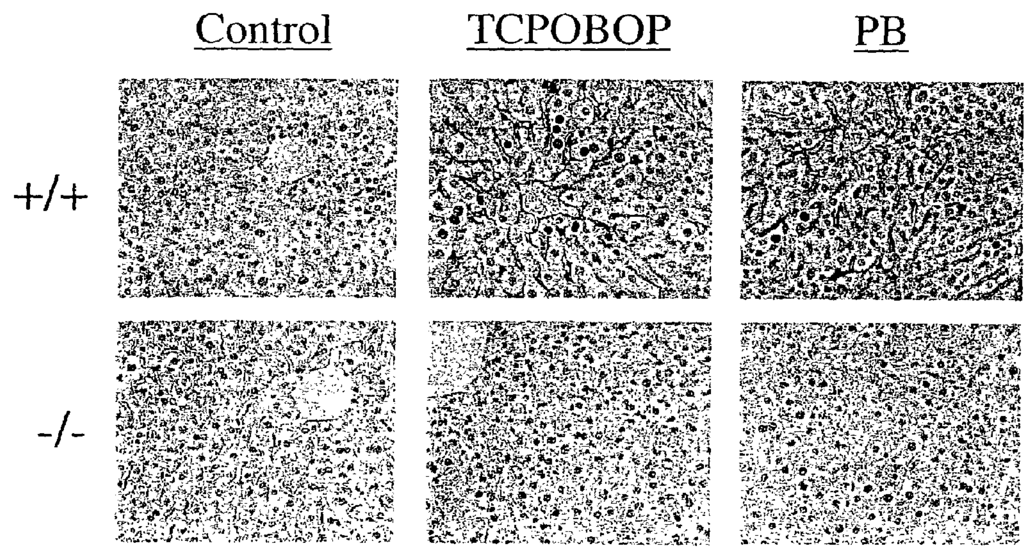
FIG. 3B is a set of pictures of PB-treated, TCPOBOP-treated, or control mice that were treated with BrdU for two hours before their liver tissues were harvested. The representative microphotography illustrates the presence of BrdU-positive hepatocytes only in PB- or TCPOBOP-treated wild-type animals.

Acute treatments with PB-like inducers, particularly TCPOBOP, cause an up to 2-fold increase in liver mass relative to total body mass. This hepatomegaly is thought to be a reflection of both cellular hypertrophy and mitogenesis. The CAR−/− mice showed no evidence of the increase in liver mass observed in the wild-type mice after 3 days of treatment with either PB or TCPOBOP (FIG. 3A). The xenobiotic induction of DNA synthesis revealed by increased incorporation of BrdU in the wild-type animals was also completely absent in the CAR−/− animals (FIG. 3B).

These results demonstrate that CAR is essential for these responses to PB-like inducers. This conclusion was confirmed and extended by examination of the effect of the loss of CAR expression on metabolism of two xenobiotics. The first is the classic substrate zoxazolamine. Many studies have demonstrated that increased CYP enzyme activity results in increased metabolic inactivation of this muscle relaxant, which is reflected in decreased duration of zoxazolamine-induced paralysis. As demonstrated in Tables 1 and 2, pretreatment of wild-type animals with either PB or TCPOBOP significantly decreased the duration of paralysis, as expected. The duration of paralysis was substantially longer in untreated CAR−/− mice than in wild-type mice, and, consistent with the results described above, the paralysis was not affected by pretreatment with either PB or TCPOBOP. For example, wild-type control female mice were paralyzed more than 12 hours, while wild-type xenobiotic-pretreated female mice were not paralyzed. Among the CAR−/− females, two animals from each group of control, PB-treated, or TCPOBOP-treated animals died; the survivors were paralyzed for more than 12 hours.

TABLE 1

Increased duration of zoxazolamine-induced paralysis in male CAR (−/−) mice due to decreased metabolism of zoxazolamine

| | CAR (+/+) | CAR (−/−) |
|---|---|---|
| Control | 2 hours | >5 hours |
| PB-treated | <20 minutes | >5 hours |
| TCPOBOP-treated | <20 minutes | >5 hours |

TABLE 2

Increased duration of zoxazolamine-induced paralysis in female CAR (−/−) mice due to decreased metabolism of zoxazolamine

| | CAR (+/+) | CAR (−/−) |
|---|---|---|
| Control | >12 hours | died |
| PB-treated | not paralyzed | died |
| TCPOBOP-treated | not paralyzed | died |

In these experiments, mice were pretreated for three days with PB or TCPOBOP, after which time they were given a single intraperitoneal injection of zoxazolamine (300 mg/kg). Paralysis time was recorded as the time when the mice were able to right themselves repeatedly.

Figure 4:
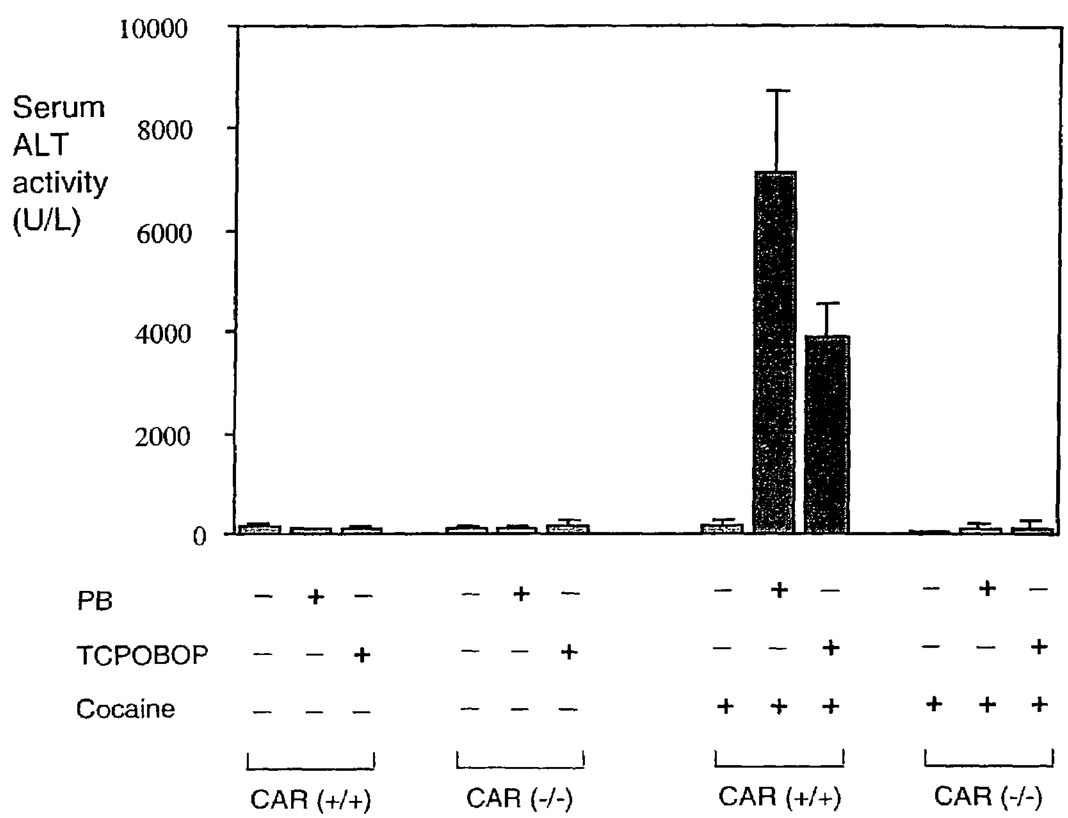
FIG. 4 is a bar graph showing the effect of PB or TCPOBOP on cocaine-mediated hepatotoxicity, measured as serum alanine aminotransferase (ALT) activity. Male mice were pretreated with PB or TCPOBOP for three days. Twenty-four hours after the last dose, one injection of cocaine was given to the animals. Blood was drawn 20 hours after cocaine treatment for determination of serum ALT activity.

Treatment with PB-like inducers also sensitizes animals to hepatotoxic effects of a number of compounds, including cocaine. As shown in FIG. 4, treatment with either PB or TCPOBOP resulted in a significant increase in serum levels of the liver enzyme alanine aminotransferase (ALT) as an acute response to cocaine administration. This evidence of liver damage was not observed in CAR−/− animals.

These results clearly demonstrated that CAR was required for response to PB-like inducers of xenobiotic metabolism, and thus CAR functioned as a xenobiotic receptor in vivo to mediate the response to PB-like inducers. CAR can therefore be added to the previously described peroxisome proliferator activated receptor α and the aryl hydrocarbon receptor as a primary determinant of the response of phase I metabolic enzymes to foreign compounds. CAR is joined in this by its closest relative within the receptor superfamily, PXR/SXR, which has recently been shown to mediate response to a distinct group of xenobiotics. Although both DNA binding specificity and xenobiotic responses of CAR and PXR/SXR have been reported to overlap to some extent, no evidence for any compensatory effect of the latter was observed in the CAR knockout animals. Thus, it is now apparent that specific xenobiotics can induce specific metabolic responses by activating distinct receptors.

This mechanism may account for a large number of clinically significant drug-drug interactions in which the presence of one compound, such as phenobarbital, results in increased metabolism of another drug or foreign compound. Differences in the levels of activation of xenobiotic receptors among individuals based on differences in exposure to specific xenobiotics may also explain the significant inter-individual variability of the levels of particular cytochromes. Consistent with the very low basal levels of mouse CYP2B10, most humans have low or undetectable levels of CYP2B6, a human target of CAR activation. However, this enzyme is present at up to 100-fold higher levels in a subset of individuals. The results described here suggest that this variability could be the basis for the relatively rare but clinically significant hepatotoxicity observed in a subset of individuals exposed to high levels of cocaine. More generally, variations in CAR activity in response to the wide range of PB-like inducers may have significant impact on the metabolism of a wide range of pharmacologic agents and other foreign compounds. The CAR mice described herein facilitate the identification of compounds able to activate CAR in vivo, as well as enable identification of additional, specific downstream target genes that mediate its effects.

The experiments described above were carried out as follows.

Targeting Vector Construction

To construct the targeting vector for the CAR locus, an Xba I-Eag I fragment containing the nuclear localized β-galactosidase gene from vector pPD 46.21 was subcloned into the Xba I and EcoR I sites of the pGKneo plasmid. DNA from AB1 ES cells was used to amplify CAR genomic fragments for both 5' and 3' arms. For the 5' arm, a 3 kb CAR promoter fragment was cloned into the Apa I and Xba I sites. For the 3' arm, a 5 kb fragment spanning exons 3 to 9 was cloned into the Sal I and Not I sites. The primers for the 5' arm were 5'-gcgcgcgggccctggcatacattaacacaaacacatacatat-3' (SEQ ID NO.: 3) and 5'-gcgcgctctagaaggacccagactctg-gacccagggcaaaga-3' (SEQ ID NO: 4). The primers for the 3' arm were 5'-gcgcgcgtcgacaggtgaagtgcttctccccaacagaaacaa-3' (SEQ ID NO: 5) and 5'-gcgcgcgcggccgctgtcctgggag-cagcctctgcagccgct-3' (SEQ ID NO: 6).

Generation of CAR Receptor Knockout Mice

AB1 ES cells ($10^7$) were electroporated with 25 μg targeting construct in 0.9 ml PBS using a Bio-Rad Gene Pulser (500 μF, 230 V). The cells were then plated on one or two 10-cm plates containing a monolayer of irradiated STO feeder cells. Twenty-four hours later, they were subjected to G418 selection (350 μg/ml, Gibco) for 9 days. Resistant clones were analyzed by Southern blotting after Hind III digestion, using the 3' probe indicated in FIG. 1A (FIG. 1B). The primers for the 3' probe were 5'-ggacaacctcagcccacagt-gatgc-3' (SEQ ID NO: 7) and 5'-tcctttggttaccacctgactctgc-3' (SEQ ID NO: 8). Two positive clones were expanded and injected into C57BL/6 blastocysts. Male chimeras were back crossed to C57BL/6 females. Heterozygotes were determined by Southern blotting and intercrossed to generate homozygotes.

Animal Treatment

At least three mice between 8–10 weeks old were used for each treatment. Mice were pretreated by intraperitoneal injection with corn oil, PB (100 mg/kg, Sigma), or TCBOPOP (3 mg/kg) for the indicated time. For the three day PB treatment, mice were injected intraperitoneally three times with PB, one injection per day.

Zoxazolamine Paralysis Test

Mice pretreated with corn oil, PB, or TCPOBOP were given a single intraperitoneal injection of zoxazolamine (300 mg/kg, Sigma) 24 hours after the last dose of PB. Mice were placed on their backs, and the paralysis time was defined as the time required for the animal to regain sufficient consciousness to right itself repeatedly (Liang et al., Proc. Natl. Acad. Sci. USA, 93:1671–6, 1996).

Cocaine Treatment and ALT Assay

Male mice pretreated with corn oil, PB, or TCPOBOP were injected intraperitoneally with cocaine HCl (30 mg/kg) 24 hours after the last dose of PB. The mice were anaesthetized 24 hours after cocaine treatment. Blood was drawn from the eye for determination of serum alanine aminotransferase (ALT) activity.

RNA Analysis

20 μg of total RNA from individual mouse livers was subjected to Northern blot analysis (FIG. 1C). A mouse CAR cDNA probe was used to reveal the absence of CAR transcripts in the CAR null mice. Probes for CYP2B10 were prepared by RT-PCR with mouse liver total RNA using Superscript One-step RT-PCR System (Life Technologies). PCR primers were 5'-ccgcctctagaagtcaacattggttagac-3' (SEQ ID NO: 9) and 5'-ccgccggatcccacactaagcctcataat-3' (SEQ ID NO: 10). For in situ hybridization, small intestine tissue was cross sectioned at 7 μM thickness. Slides were subjected to in situ hybridization with a [$^{35}$S]-labeled CYP2B10 antisense probe. To prepare the probe, the CYP2B10 RT-PCR product was subcloned into the Xba I and Bam HI sites of Bluescript® SK(−) phagemid (Stratagene). The plasmid was linearized with Xba I. T7 RNA polymerase was used to synthesize [$^{35}$S]-labeled antisense probes.

Determination of Proliferation of Hepatocytes Following PB or TCPOBOP Treatment

Mice pretreated with corn oil, PB or TCPOBOP received a single intraperitoneal dose of BrdU/FdU (2 ml/100 g, Amersham). Mice were sacrificed 2 hours after BrdU administration. BrdU incorporation was determined using a mouse anti-BrdU monoclonal antibody (DAKO Corporation) and Vectastain ABC Kit (Vector Laboratories Inc.) (FIG. 3B), using standard procedures.

Generation of Mice Expressing a Human CAR Receptor

It is known that the ligand binding domains of human and mouse CAR genes differ somewhat in amino acid sequence, and that these two proteins respond differently to some activators. In particular, TCPOBOP is an agonist ligand for the murine CAR receptor, but not the human CAR receptor (Tzameli et al., supra). Similarly, clotrimazole is an inverse agonist for the human, but not the murine, CAR receptor (Moore et al., supra). As a result, CAR−/− knockout mice expressing a functional human CAR receptor also provide useful models for drug screening since their response to drugs or other xenobiotic compounds should be based on the human rather than the murine CAR receptor. Such "humanized" CAR mice allow for the identification of compounds, such as those in clinical development, with potentially undesirable effects in humans, which may not be evident in mice.

A humanized CAR mouse lacking the murine CAR but expressing the human CAR receptor may be generated by any of several standard methods (see, for example, Ausubel et al. (Chapter 9), supra). For example, a conventional transgenic animal expressing the human CAR gene from a promoter active in appropriate tissues, such as the liver, may be generated. Examples of such promoters include those directing expression of albumin (Xie et al., Nature 406: 435–439, 2000), transthyretin (Ye et al., Mol Cell Biol. 19:8570–8580, 1999), or CAR itself. This human CAR transgene may then be introduced into a homozygous CAR−/− mouse by conventional breeding (Pierson et al., Mol Endocrinol. 14:1075–1085, 2000; Slee et al., Proc Natl Acad Sci USA. 96:8040–8045, 1999). In another possible method, the human CAR transgene may be injected into fertilized oocytes from homozygous CAR−/− mice, directly generating the desired transgenic mice. In a third method, embryonic stem cells may be generated from a homozygous CAR−/− animal (Ausubel et al. (Chapter 9), supra). Conventional homologous recombination techniques may then be used to replace the inactivated murine CAR gene with a functional human CAR receptor gene (Fiering et al., Methods Enzymol. 306:42–66, 1999). Since the CAR−/− animals contain the neo gene which confers resistance to G418, another appropriate gene such as hygromycin may be used in the human CAR replacement construct to allow the selection of cells in which the human CAR gene has replaced the inactivated murine CAR gene. In still another possible method, a functional human CAR receptor gene may be introduced into a homozygous CAR−/− mouse using gene therapy and a promoter active in appropriate tissues, such as the promoters described above, and contained in an adenoviral, adeno-associated viral, retroviral, lentiviral, herpes viral, nonviral, or any other suitable vector (see, for example, Sarkar et al., Hum Gene Ther. 11:881–894, 2000; Goddard et al., Gene Ther. 4:1231–1236, 1997).

Assays for CAR Receptor Activity

The homozygous CAR−/− animals described herein are useful for drug metabolism assays since they allow the identification of drugs or other xenobiotic compounds that induce expression of CYP2B10 or other CAR target genes in wild-type, but not CAR−/− animals. The detection of CYP2B10 induction may be performed by any of several assays, including assays of CYP2B10 protein levels (for example, by Western blot analysis), mRNA levels (for example, by Northern blot analysis), or enzymatic activity (for example, my measuring 7-pentoxyresorufin O-dealkylase enzymatic activity as described, for example, in Pellinen et al. (Hepatology 23:515–23, 1996)). Alternatively, an increase in liver mass relative to total body mass or an increase in DNA synthesis in the liver may be measured as described herein. Similar assays for other CAR target genes may also be used.

Moreover, as alternatives to assays involving endogenous murine CAR target genes, assays may be conducted to measure appropriate reporter transgenes inserted by any standard technique (for example, those techniques described above) into wild-type mice, CAR−/− mice, humanized CAR mice, mice lacking the gene encoding the receptor related to CAR (known as SXR, PXR or by other names (Kliewer et. al., Cell 92:73–82, 1998; Blumberg et al., Genes Dev. 12:3195–3205, 1998)), or any other appropriate strain. These reporter transgenes consist of a CAR responsive promoter operably-linked to an easily measured reporter gene. Examples of appropriate promoters include native CYP promoters such as the CYP2B10 promoter containing the previously described phenobarbital response element (Honkakoski et al., supra) or the CYP2B6 promoter or synthetic promoter constructs in which DNA binding sites for CAR/RXR heterodimers are linked to functional basal promoters (Tzameli, et al., supra). Examples of appropriate reporter genes include, without limitation, human growth hormone, secreted alkaline phosphatase, luciferase, green fluorescent protein, chloramphenicol acetyl transferase, CYP2B6, and any other reporter gene (see, for example, Ausubel et al. (Chapter 9), supra). The assays for CAR target genes involve standard procedures (see, for example, Ausubel et al. (Chapter 9), supra) and may be based on appropriate samples from the mice, such as liver or serum samples. Alternatively, hepatocytes or other appropriate cell types may be harvested from the animals and propagated. Compounds may be administered to these cells to determine whether the compounds effect a change in expression of CAR target genes or reporter transgenes.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

The invention claimed is:

1. A screening method for determining whether a compound activates a human CAR receptor, said method comprising the steps of:

(a) administering a compound to a transgenic mouse whose genome comprises a transgene comprising a nucleic acid sequence encoding a human CAR receptor encoded by SEQ ID NO: 2 or a functional variant thereof having at least about 95% sequence identity to the amino acid sequence encoded by SEQ ID NO: 2 operably linked to a promoter, wherein expression of said nucleic acid sequence results in the production of a human CAR receptor in the liver of said mouse, wherein the human CAR receptor induces expression of a CAR target gene, and wherein the genome of said mouse comprises a disruption of the endogenous mouse CAR receptor gene, wherein said mouse lacks production of functional endogenous mouse CAR receptor, and (b) measuring induction of a CAR target gene, whereby said compound is determined to activate said CAR receptor if said compound mediates induction of said CAR target gene.

2. The method of claim 1, wherein step (a) further comprises administering clotrimazole, a human CAR receptor inverse agonist, to said mouse expressing said human CAR receptor.

3. A screening method for determining whether a compound inhibits a human CAR receptor, said method comprising the steps of:

(a) administering a compound to a transgenic mouse whose genome comprises a transgene comprising a nucleic acid sequence encoding a human CAR receptor encoded by SEQ ID NO: 2 or a functional variant thereof having at least about 95% sequence identity to the amino acid sequence encoded by SEQ ID NO: 2 operably linked to a promoter, wherein expression of said nucleic acid sequence results in the production of a human CAR receptor in the liver of said mouse, wherein the human CAR receptor induces expression of a CAR target gene, and wherein the genome of said mouse comprises a disruption of the endogenous mouse CAR receptor gene, wherein said mouse lacks production of functional endogenous mouse CAR receptor, and (b) measuring expression of a CAR target gene in the presence and absence of said compound, whereby said compound is determined to inhibit said human CAR receptor if said compound decreases said expression of said CAR target gene.

4. The method of claim 3, wherein step (a) further comprises administering a phenobarbital-like inducer to said mouse expressing said human CAR receptor.

5. The screening method of claim 4, wherein said phenobarbital like inducer is administered after said compound.

6. A screening method for determining whether a compound modulates the activity of a human CAR receptor, said method comprising the steps of:

(a) administering a compound to a transgenic mouse whose genome comprises a transgene comprising a nucleic acid sequence encoding a human CAR receptor encoded by SEQ ID NO: 2 or a functional variant thereof having at least about 95% sequence identity to the amino acid sequence encoded by SEQ ID NO: 2 operably linked to a promoter, wherein expression of said nucleic acid sequence results in the production of a human CAR receptor in the liver of said mouse, wherein the human CAR receptor induces expression of a CAR target gene, and wherein the genome of said mouse comprises a disruption of the endogenous mouse CAR receptor gene, wherein said mouse lacks production of functional endogenous mouse CAR receptor, and (b) measuring a physiological effect mediated by the administration of said compound, whereby said compound is determined to modulate the activity of said human CAR receptor if the magnitude of said physiological effect in said mouse expressing said human CAR receptor differs from a magnitude of said physiological effect in a mouse null for any CAR receptor activity.

7. The method of claim 6, wherein said measuring said physiological effect comprises measuring the toxicity or activity mediated by the administration of said compound or measuring the half-life of said compound.

8. The method of claim 7, wherein said toxicity or activity is mediated by a metabolite of said compound.

9. A screening method for determining whether the metabolism of a compound is regulated by modulation of the activity of a human CAR receptor, said method comprising the steps of:

(a) administering a compound to a transgenic mouse whose genome comprises a transgene comprising a nucleic acid sequence encoding a human CAR receptor encoded by SEQ ID NO: 2 or a functional variant thereof having at least about 95% sequence identity to the amino acid sequence encoded by SEQ ID NO: 2 operably linked to a promoter, wherein expression of said nucleic acid sequence results in the production of a human CAR receptor in the liver of said mouse, wherein the human CAR receptor induces expression of a CAR target gene, and wherein the genome of said mouse comprises a disruption of the endogenous mouse CAR receptor gene, wherein said mouse lacks production of functional endogenous mouse CAR receptor, and (b) measuring the rate of metabolism of said compound, whereby said metabolism of said compound is determined to be regulated by modulation of the activity of said CAR receptor if said rate of metabolism is faster in said mouse expressing said human CAR receptor than a rate of metabolism in a mouse null for any CAR receptor activity.

10. The method of claim 9, wherein said measuring said rate of metabolism comprises measuring toxicity or activity mediated by the administration of said compound, measuring half-life of said compound, or measuring serum level of a liver enzyme.

* * * * *

SEQUENCE LISTING

```
<160> NUMBER OF SEQ ID NOS: 27

<210> SEQ ID NO 1
<211> LENGTH: 358
<212> TYPE: PRT
<213> ORGANISM: Mouse

<400> SEQUENCE: 1

Met Thr Ala Met Leu Thr Leu Glu Thr Met Ala Ser Glu Glu Glu Tyr
1               5                   10                  15

Gly Pro Arg Asn Cys Val Val Cys Gly Asp Arg Ala Thr Gly Tyr His
            20                  25                  30

Phe His Ala Leu Thr Cys Glu Gly Cys Lys Gly Phe Phe Arg Arg Thr
        35                  40                  45

Val Ser Lys Thr Ile Gly Pro Ile Cys Pro Phe Ala Gly Arg Cys Glu
    50                  55                  60

Val Ser Lys Ala Gln Arg Arg His Cys Pro Ala Cys Arg Leu Gln Lys
65                  70                  75                  80

Cys Leu Asn Val Gly Met Arg Lys Asp Met Ile Leu Ser Ala Glu Ala
                85                  90                  95

Leu Ala Leu Arg Arg Ala Arg Gln Ala Gln Arg Arg Ala Glu Lys Ala
            100                 105                 110
```

```
Ser Leu Gln Leu Asn Gln Gln Gln Lys Glu Leu Val Gln Ile Leu Leu
        115                 120                 125

Gly Ala His Thr Arg His Val Gly Pro Leu Phe Asp Gln Phe Val Gln
    130                 135                 140

Phe Lys Pro Pro Ala Tyr Leu Phe Met His His Arg Pro Phe Gln Pro
145                 150                 155                 160

Arg Gly Pro Val Leu Pro Leu Leu Thr His Phe Ala Asp Ile Asn Thr
                165                 170                 175

Phe Met Val Gln Gln Ile Ile Lys Phe Thr Lys Asp Leu Pro Leu Phe
            180                 185                 190

Arg Ser Leu Thr Met Glu Asp Gln Ile Ser Leu Leu Lys Gly Ala Ala
        195                 200                 205

Val Glu Ile Leu His Ile Ser Leu Asn Thr Thr Phe Cys Leu Gln Thr
    210                 215                 220

Glu Asn Phe Phe Cys Gly Pro Leu Cys Tyr Lys Met Glu Asp Ala Val
225                 230                 235                 240

His Ala Gly Phe Gln Tyr Glu Phe Leu Glu Ser Ile Leu His Phe His
                245                 250                 255

Lys Asn Leu Lys Gly Leu His Leu Gln Glu Pro Glu Tyr Val Leu Met
            260                 265                 270

Ala Ala Thr Ala Leu Phe Ser Pro Asp Arg Pro Gly Val Thr Gln Arg
        275                 280                 285

Glu Glu Ile Asp Gln Leu Gln Glu Glu Met Ala Leu Ile Leu Asn Asn
    290                 295                 300

His Ile Met Glu Gln Gln Ser Arg Leu Gln Ser Arg Phe Leu Tyr Ala
305                 310                 315                 320

Lys Leu Met Gly Leu Leu Ala Asp Leu Arg Ser Ile Asn Asn Ala Tyr
                325                 330                 335

Ser Tyr Glu Leu Gln Arg Leu Glu Glu Leu Ser Ala Met Thr Pro Leu
            340                 345                 350

Leu Gly Glu Ile Cys Ser
        355


<210> SEQ ID NO 2
<211> LENGTH: 348
<212> TYPE: PRT
<213> ORGANISM: Human

<400> SEQUENCE: 2

Met Ala Ser Arg Glu Asp Glu Leu Arg Asn Cys Val Val Cys Gly Asp
1               5                   10                  15

Gln Ala Thr Gly Tyr His Phe Asn Ala Leu Thr Cys Glu Gly Cys Lys
            20                  25                  30

Gly Phe Phe Arg Arg Thr Val Ser Lys Ser Ile Gly Pro Thr Cys Pro
        35                  40                  45

Phe Ala Gly Ser Cys Glu Val Ser Lys Thr Gln Arg Arg His Cys Pro
    50                  55                  60

Ala Cys Arg Leu Gln Lys Cys Leu Asp Ala Gly Met Arg Lys Asp Met
65                  70                  75                  80

Ile Leu Ser Ala Glu Ala Leu Ala Leu Arg Arg Ala Lys Gln Ala Gln
                85                  90                  95

Arg Arg Ala Gln Gln Thr Pro Val Gln Leu Ser Lys Glu Gln Glu Glu
            100                 105                 110

Leu Ile Arg Thr Leu Leu Gly Ala His Thr Arg His Met Gly Thr Met
```

-continued

```
        115                 120                 125

Phe Glu Gln Phe Val Gln Phe Arg Pro Pro Ala His Leu Phe Ile His
    130                 135                 140

His Gln Pro Leu Pro Thr Leu Ala Pro Val Leu Pro Leu Val Thr His
145                 150                 155                 160

Phe Ala Asp Ile Asn Thr Phe Met Val Leu Gln Val Ile Lys Phe Thr
                165                 170                 175

Lys Asp Leu Pro Val Phe Arg Ser Leu Pro Ile Glu Asp Gln Ile Ser
            180                 185                 190

Leu Leu Lys Gly Ala Ala Val Glu Ile Cys His Ile Val Leu Asn Thr
        195                 200                 205

Thr Phe Cys Leu Gln Thr Gln Asn Phe Leu Cys Gly Pro Leu Arg Tyr
    210                 215                 220

Thr Ile Glu Asp Gly Ala Arg Val Gly Phe Gln Val Glu Phe Leu Glu
225                 230                 235                 240

Leu Leu Phe His Phe His Gly Thr Leu Arg Lys Leu Gln Leu Gln Glu
                245                 250                 255

Pro Glu Tyr Val Leu Leu Ala Ala Met Ala Leu Phe Ser Pro Asp Arg
            260                 265                 270

Pro Gly Val Thr Gln Arg Asp Glu Ile Asp Gln Leu Gln Glu Glu Met
        275                 280                 285

Ala Leu Thr Leu Gln Ser Tyr Ile Lys Gly Gln Gln Arg Arg Pro Arg
    290                 295                 300

Asp Arg Phe Leu Tyr Ala Lys Leu Leu Gly Leu Leu Ala Glu Leu Arg
305                 310                 315                 320

Ser Ile Asn Glu Ala Tyr Gly Tyr Gln Ile Gln His Ile Gln Gly Leu
                325                 330                 335

Ser Ala Met Met Pro Leu Leu Gln Glu Ile Cys Ser
            340                 345


<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3

gcgcgcgggc cctggcatac attaacacaa acacatacat at                        42


<210> SEQ ID NO 4
<211> LENGTH: 42
<212> TYPE: DNA
<213> ORGANISM: Artificial Sequence
<220> FEATURE:
<223> OTHER INFORMATION: Primer

<400> SEQUENCE: 4

gcgcgctcta gaaggaccca gactctggac ccagggcaaa ga                        42


<210> SEQ ID NO 5
<211> LENGTH: 42
<212> TYPE: DNA
<213> ORGANISM: Artificial Sequence
<220> FEATURE:
<223> OTHER INFORMATION: Primer

<400> SEQUENCE: 5

gcgcgcgtcg acaggtgaag tgcttctccc caacagaaac aa                        42
```

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
gcgcgcgcgg ccgctgtcct gggagcagcc tctgcagccg ct 42

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ggacaacctc agcccacagt gatgc 25

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
tcctttggtt accacctgac tctgc 25

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
ccgcctctag aagtcaacat tggttagac 29

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
ccgccggatc ccacactaag cctcataat 29

<210> SEQ ID NO 11
<211> LENGTH: 1822
<212> TYPE: DNA
<213> ORGANISM: Mouse

<400> SEQUENCE: 11
accaggacca tggagcccag tgtgctgctc ctccttgctc tccttgtggg cttcttgcta 60
ctcttagcca ggggacaccc aaagtcccgt ggcaacttcc caccaggacc ccgtcccctg 120
cccctcttgg ggaacctctt gcagatggac agaggaggcc tcctcaagtc tttaattcag 180
cttcgagaaa aatatggcga tgtgttcaca gtgcacctgg gaccaaggcc tgtggttatg 240
ctgtgtggaa cagacaccat aagggaggct ctggtgggcc aagccgaggc tttctctggc 300

-continued

```
cgggggacag ttgctgtcgt tgagccaacc ttcaaggaat atggtgtgat ctttgccaat    360
ggggaacgtt ggaagaccct tcgtagattc tctctggcca ccatgagaga ctttgggatg    420
ggaaagagga gtgtggagga gcggattcag gaggaagccc aatgtttagt ggaggaactg    480
cggaaatccc agggagcccc cctggacccc acgttcctct tccagtgcat cacggccaat    540
gttatctgct ccattgtgtt tggagagcgc tttgagtaca cagaccgtca gttcttgcgc    600
ctgctggagc tgttctatca gaccttttca ctcataagct cattctccag ccagatgttt    660
gagctcttct ctggcttcct gaagtacttt cctggtgccc acagacaaat ctccaaaaac    720
ctgcaggaac tcctcgacta cattggccat agtgtggaga ggcacaaggc caccttggac    780
cccagtgttc cacgagactt cattgatatt taccttctgc gcatggagaa ggagaagtcc    840
aaccagaacg cagagttcca tcaccagaac ctcatgatgt ctgtgctctc tctcttcttt    900
gtcggcaccg agaccagcag caccacgctc cactatggct tcctgctcat gctcaagtac    960
ccccatgtta cagagaaagt ccaaaaggag attgatcagg tgatcggctc acaccggcta   1020
ccaacccttg atgaccgcac caaaatgcca tactcagatg cagtcatcca cgagattcag   1080
agattttcag atcttatacc tattggagtg ccacacagag tcaccaaaga taccctgttc   1140
cgagggtacc tgctccccaa gaacactgag gtgtacccca tcctgagttc agctctacat   1200
gatccacagt actttgaaca accagacagt ttcaatcctg accagttcct ggatgccaat   1260
ggggcactga agaaaagtga agcttttctg cccttctcaa caggacaaat tttgatcaa    1320
aagtctgtgg gaaagcgcat ttgtcttggt gaaagcattg cccgcagcga attgttcctt   1380
ttcttcacgt ccatcctcca gaacttctct gtggcaagcc atgttgctcc taaggacatt   1440
gacctcactc ccaaggagag tggtattgga aaaatacctc caacgtacca gatctgcttc   1500
ttggcccgct gattgggctg aggcagacag gggtcaccag taatgttgag aatgactctg   1560
tctttgagcc tctgagacag ctggtggaaa tcagtactcc tattgcatgt ctccaaatct   1620
ccagggctcc aaggcatgtt cttcttccct gtgaatggca ctggagaaat caatcaactg   1680
tctttcttga catgtgaaaa gagacttctg gagtccacat ctcatgttga gtcacttccc   1740
ttttcctccc aatagcccaa gtgtccactt atcagctccg catgatctgg gatctgtgct   1800
aatggactct gtataaggtc tg                                            1822
```

<210> SEQ ID NO 12
<211> LENGTH: 42547
<212> TYPE: DNA
<213> ORGANISM: Human

<400> SEQUENCE: 12

```
gatccagggg tctgccgtag atcttagcca tggactgcac ctggggctcc gtttgaagaa     60
ctatttgtag ttttacagct tcaattctgg aagagacaaa cttaacaagg aggttaaaga    120
cacagggatt gaaatgtctg gcctgaagtg caggggatta tttctttggc acacttcaca    180
ggccctgact acctgcttga tagttttgaa aaggcctggt ccagcaaata atgatttggc    240
cattggatgg gtgctatcaa cgcctaaatg aaaggtttgg tgaagggttt taagtaattt    300
ccattggtta gctgcaggca aaagtatttt tccttctttg gtggctagac atcctgaggg    360
gagggaacta tgtccttgtg aggtacccca ttctatttct tctgctgagc actggggctt    420
ggtttcctgg aggggattac cccatactag ggttccttct ataagcattt ctaatggagg    480
gtcccgcctt gtggctcttt ggcttcaata tctgcttggt ggttcccttc tatttccctt    540
tcctttcctt tctgatgacc ccagcagtgt aagatggcca cctctttagg tttccgtaca    600
```

-continued

```
gcccataata actcataatg gcttcctgat gtttaatagg tgttccctca gaagttagga    660
attccatttc tcaccatatt tttgtgtagg catggaggag aaggtaagca taattagagt    720
gtttatatat atttaccctt ttcccttctc ctaattctag tgtatcatgg cccctgcttt    780
tgctaggatg tctctcccta acaaaggagt ggggctttca ggcataatta gaaaggcatg    840
tgaaaagagt aaagtccccc agttacaact tagtggctgg gcgaagtaac tagtgactgc    900
ttgtcctagg acccctcgga tagtaacaga tctggaaatc cagctagtcc tgtctctcaa    960
aactacaatg ataaacaata agagaaaaag aaaggaagaa aggatataca tacataaaga   1020
agccaactaa taatatgaca ggattaagct ctcacatatc aataataacc ttgaattaaa   1080
tggattaaac tttccactta aaagaaagag actggctgaa tggatttaaa aagcatgacc   1140
cagctatatg ctgcctacaa gaaacacatc tcaccaggaa agacatatat agtgaaagta   1200
aagaaatgag aaaagatatt ccatgcaaat aaaaaccaaa agtgagcagc aatacctatg   1260
tttataaagg aaacagactt taagtcaaaa actgtaaaaa gagacaaaga aggtcaatac   1320
ataatgataa aaggatcaat cgagcaaagg atccatgagg aaattcctgc ctaataaatt   1380
ttggtcagac cggttgtctg ctctcaaacc ttgtctcctg ataagatgtt atcaatgaca   1440
atgcttgccc gaaacttcat tgcaatttta atttcacccc ggtcctgtgg tcctgtgatc   1500
tcgccctgcc tccatttgcc ttgttatatc ttattacctt gtgaagcatg tgatctctgt   1560
gacctacacc ctattcgtac actccctccc cttttgaaaa tcactaataa aaactttctg   1620
gttttacggc tcagggggca tcatggaacc tgccgacatg tgatgtctcc cccggacccc   1680
cagctttaaa atttctctct tttgtgctct gtccctttat ttctcaggct ggccgacact   1740
tagggagaac agaaaagaac ctacgtggaa tattgggggt gaattttgcc cgatatctgg   1800
ctgaatttcc cctgataatg ccactctcta tgtccatgtg tacacattgt ttagcaccca   1860
cttatgaatg agaacatgtg atattcactt tctgtgcctg gcttgtttca cttaagataa   1920
tcccctccag ttgtatccat gttgctataa aagacattat tttattcctt tttatggcta   1980
aatagtattc aatggtgtat atataccaca ttttatttaa ccattcatct gttgattccc   2040
tatttttgct attgtaaata gcatttggac cacatttcaa gtacttaatt agtggccaca   2100
tgcagcaagt gactatcaca ttggacaatg tagccccaac ccactgtatg accttgggta   2160
agacttgcaa actgtcattg cttcaatatc tccatctata aaatggggat ggcaacaata   2220
cctcactaag agtgtaaaga ctgagttact gtgtgtaaag cacttcacgc ctccccatcg   2280
gtgcttcacc ctggggctgc aatgagcacc caatcttagt gtcagatgac acagcacagc   2340
aagaccgagg cccttggttc aggaaagtcc atgctgccac ctcttcaggg tcaggaaagt   2400
acagtttcca cctcttacaa ataggactgt ttgtctgctc ctcctgggtc aaagtaactt   2460
cgggttcagg tcctggatcc agcaaagggt ttgcttaaca ttgcaagaaa gatgttgcct   2520
catggtcaaa agtcaggcgt aggatgagac aggcagacac gcacacattc acacccacgt   2580
tttgcaaaga tggactgacc ctgtcagagg atgtgtgggt gaaggtgcac agtgaggata   2640
gagacatatg ggagtccagt agacatcaat caaactggac tcagtttgca cacacctgga   2700
gctcaagagt ctccaggggg aaaacagaga cacaaagtca gacagagaga gagccagaga   2760
aatttcctgc accgtgaaga tagtcagagg cagggaagaa actccttagc actagttaga   2820
gtgatcagaa accaagagga cctgatcgct gtacctgcca ggtctcagtt tctgtctcct   2880
tccaactgac cacctcttcc tctgagactc accagttctg catctcttgc tcctccttct   2940
```

-continued

```
gtttctccga ccacttccac ctgtggctgt cacagaaggg cggatgaagg aggggacact   3000
ggagatagac tcagcatctg caggcttcca aagagagggg ctaggagatc caccaacaca   3060
ccagcacaaa tacaccagca cacacagata cacacaattg gttcatgtat tgctaggtta   3120
cagtttgcta tgctacaaag gcagtaggcc aaatttgatt gaattgaata attccttatt   3180
ttcatcagct tctccttttt tttttttttt tttttttttt gagatggagt attgctgtgt   3240
cacccaggct ggagtgcagt ggtgtaatct tggctcactg cagcctccac ctcccaggtt   3300
caagtgattc tcttgcctca gcctcccgag tagctgggat taaaagtacc caccatcacg   3360
cccggttaat ttttgtgttt ttagtacaga tggggttttg ccatgtgggc caggatggtc   3420
tcgaactctt gacctcaatt gatctgcccc cctcagcttc ccaacgtgct gggattacag   3480
gtgtgagcca ccgcacccag ccagcctctc agttttgaac atgcactacc accacctcca   3540
caacacacaa atgtaaatgc actttcgtat ataaaactgt ataaatacaa ggaagctcat   3600
acacatgcaa ggatacacac ataagcaccc ccagattcaa ccacagaaat atacgccagt   3660
acatttgcat aaattcaaac accccttac atgtaaaaat catataagca catacaggga   3720
tgcaagcagg catggacaaa tgcatgcaag cacagacaaa cagacaaagc taagtaaaaa   3780
agtgcaagct cacctatgct tacaaaaata gacatacata tacccacaaa cccacacacc   3840
cacacattca cttgctcacc tggactttga tatctctacc actgtatccc tgccaatatc   3900
tacagagtgg gtaaagggat aggcatcagg tcactgggtt gcccaagcag gaagtctggg   3960
ttccctaaca actttttcta agctaatgct cctggatgat gatgaaaaag gaggtgggga   4020
atggatgaaa ttttataaca gggtgcagag gcagggtcag gataaaaggc ccagttggag   4080
gctgcagcag ggtgcagggc agtcagacca ggaccatgga actcagcgtc ctcctcttcc   4140
ttgcactcct cacaggactc ttgctactcc tggttcagcg ccaccctaac acccatgacc   4200
gcctcccacc agggccccgc cctctgcccc ttttgggaaa ccttctgcag atggatagaa   4260
gaggcctact caaatccttt ctgagggtaa gacacagacg aatggggtct gagggtgagc   4320
tgcttcttgc cttggtactt ggggaagctt caccaaacag aatgaggcag acttccagag   4380
tcaggggtgg cacgggcatg gttggtgagt acggagcatg gtgaagcatg atgggtggta   4440
ttattaggag aaaagcatca aattaaattt agcagagttt atttgagcaa agaagtgact   4500
catgagttgg acagctccct aaaccaggaa agacaccaca cggcagtatg gtcaagtggt   4560
atttacaggc agaaaaagga ggtgacatac agaaacagcc tgattggcca cagatcacag   4620
cttgccttac ttggtcacaa tctgagcagt ttgcagcctg tgtggactga aagcccagct   4680
gctctgatta gccaacactt ggctacttgt cacaagaata tattcatttg ggccaggtgc   4740
agtggctcat gcctgtaatc ccagtgcttt tggaggccga ggtggtggat cacctgaggt   4800
caggagttcg agaccagcct ggccaacatg gtgaaacctt gtctctacta aaaatacaaa   4860
tattagctgg gcatagtgat gcgtgcctgt aatctcagct acccaggagg ctgaggaagg   4920
agaatcactt gaatccagga ggcagaggtt gcagtgagcc aaaatcttac cactgcactc   4980
catcctgggt gacagagtga gactccttct caaaaaaaaa aaaaaaaaaa agaatatact   5040
cccaagttag gttgcagttc actctacaga gagagcttta ggtcaaattt aatttaatta   5100
aacaattctc ccctttggt cagcctcaaa attttgagat tgaccaaaac cttgggcatc   5160
aacattactt ctgtcaccat cataatggac ttgtctgctc tcagtatgga attcacaatg   5220
gacaatgtca acgtagttga gtgattcttt accttttctt catgtttttg ttgttcccac   5280
tgtaatgagc ccactggatg tacaaagaat ggctgcatat gagcatttaa gactcttttt   5340
```

-continued

```
ttttctgaga cagggcctca ctctgtcagc caggctgaag tgctgtggca tgatcacgtc   5400
tcactgcagc cttgacctcc caaggctcaa gtgatcctcc tgcctcagcc ccccaagtag   5460
ctggaactac aggtgcatgc caccacgccc agctaatttt tgtatttttt gtagagacag   5520
ggttttgcca tgttgcccag actggtctta aactcctggg ctcaagcaat ccacctgcct   5580
cggcctccca aagtgctagg attacatgtg tgagccaccg cacccggcca agactcttga   5640
gaaaatacaa cacatcaggg agactgttat gatggctctc aggagggtaa tacgaagaaa   5700
atgaagtcac tgggcctgta ataaactttg aggaatgtgg acttgggggt atagataagg   5760
tccactgtcc acagagagaa gaaaggctgt taatagtctc ttttaacttg agtgtgtcca   5820
tgaaccaaac tgatcaaaat cgaataattc gaagttcaga caataaagat agttcaatag   5880
tattagagtc caattggtca tagattttgt tcagggcatg atggtaatta aggaccagag   5940
cttgctataa aataacttga tttatagaga cattcatttg tagttggcct ggtaacatat   6000
agtatcctgg agacccacta gaagaaacat taagagtaga aaagtttggg atagccaggc   6060
ttgctgtgtt agtccattct cacactgtta taaagacata cctgagactg ggtaatttat   6120
aaacaaaagg gatgtaactg actcacagtt ccacatggct ggggaggccc caggaaaata   6180
caattcatgg caaaaggtga atgagaagca ggaaacttac aatcatgatg gaaggtgaag   6240
gagaagcaag taccttcttc acaaggtggc aggaaaaaga gagagagcca agggggaaga   6300
gcctcttata aaaccatcag atcttgtgag aactcactca ctatcacaag aacagcatgg   6360
gggaaaccgc ccccaggatc cagttacctc ctactaggtc cttccctcca cacctgggga   6420
ttacaattca agatgagatt tgggtgagga cacagagcca aaccatatca cttaccatca   6480
ccattcagga tgcttgcaaa ccaactgcta gctgcacctg taaacacata tctgtttctt   6540
tcccctgaga aatgtcctta gtgtatttgt ggcagtgtct agagaaacag cagtgtcagc   6600
cgcattttaa attaagttat ctgcactagt gaattcactg gaaagataag agcaatattt   6660
ggttttcttc agcaccatac acaagcctcc aagatgggca tagaggagat ctaaaattgc   6720
gtgatgttcc attaagcgtt tttgttgcca caaatgttct catctcagtt tggagagtgg   6780
cttctaccca tctgaactcc ttggaggttc aattagctgc aaaattcaag atgtccctta   6840
atgtataact tagcctcaga ttccatacaa ctgtcaccca aataccacca agaatgagca   6900
cccaggaacc caactggaac cttttctgaa cagaaaccaa cttatcttcg tcgattttga   6960
ggttgatagt aatttcagtt attgactgtt ttggctttta actatgggag gtattaggaa   7020
actctcaggg aaacaatttg gaaagcagca gtgagctagg ccaaatagca agttctggac   7080
ctgtgaggag aaagaacaga gtaagcaaac ctcaagatac tcaaggtagg cactcgtggt   7140
gttggaaaag agggtcacct actggcatta gagcagagat cagttagatt tgtttaccca   7200
taagtctgca tagctcctga acaaggtggg aaacttactt ttttgtggtc tttttctagc   7260
atgctgcgaa ggtgcataac cacatttagt tggaaagaga ctttactgta tttacttatt   7320
tatttgtttt taatagagtt ggggtcgtgc tatgttgaac tcttggcctc aagcaatcct   7380
cccatctcaa tctcccaaag tgctgggatt acaagcatga gccaccatgc ctggccactt   7440
tacatattta atccagtaac attacacacg caattgccca caccccata ggtagtcccc   7500
aggtcttgca tacgggatgc ctggaagcaa aatatgcctt ttgcagccat tattcagata   7560
catttcctat atttagtagt gattatgtta ttagctagtt aatagtatgt tattacgtac   7620
tgttattata ttaactaact aataacataa tcactactaa atatttccag tgagtgcaaa   7680
```

-continued

```
aaagcaagtg gcaatgatgt ctagaatatc aagatatagc tttccactcc tcctttgggg   7740
tttctgggtg attctcattg ggaacatgaa gaggcattgg caccagtgaa attatttcct   7800
gattttgggg cgttggttca gaaactcaac aactccttgt tttttttgtt tgtttgcttg   7860
ttttgctaga gtataagcct ttgctaaagc cattcacaga ttatagtcct atggattttc   7920
ttgtaaggaa agggaaaggg ttaggacagc aagaaatggg gaagaaagga taaaagataa   7980
tgctttcatg atggaagaga aatcttgatc cacaatcttg gaaaagctgt ccgcatataa   8040
gatgccaact gcttctgggg aaaaacttcc ctggtcagct ttgccttaag gtctccaaca   8100
gacatacagt tctaggagtc tagaagggtc ctttccaatg gagagatgtg gatccaagat   8160
ccgagaccct gacattttgc tacagagaag aacttggcat tgtccttccc aatggagtac   8220
aaggaacagt cttagaagaa cttggtacgg tctcttccaa tggagttcaa ggacagtttg   8280
tctggtgtca tttccaaagg gcccaacctc taaattctag atcatgaaag gtctggttgt   8340
catcaaccga tgtgtcatca atgactcatt ttacctggtg aaaacatgct ttggcataaa   8400
gtattatagc cttgcattat tgagtcatat cagagtttat aagagtggga gatacatgag   8460
attctattat taggggcata ggccctctat tactatttta caagagatct atctatgtct   8520
ttccagtagg agtggatctg attgccatca atcaataata cctgagacca agggactcca   8580
atcaattcag catgctttgc ctaatgatat ttgtttgtaa tactgttgcg ggacaatcaa   8640
agactggaga gaccaaaaaa ggttcaggag agtttattaa attaaggtga tcaccggttc   8700
agccagacat acatccagaa agtctgagcc ccgaacaaag gcttttccta cttttaaaca   8760
tattaaggtg ggaactacat gaggcaggaa gccagtttca gaagtgagaa acaaagcagt   8820
taaataacat ttcttacatc ttgagaaaga catgtcttgc aacctaacct tatcggtccg   8880
gtgaccctgc agctgtgcag gaactcactg ggcctgtaat aaactttgag ggatgtggag   8940
ttggggagta taggtaaggt ccactgtcca cagagagaag acaggctgtt aatattctct   9000
tttaacttga atgtaaggtg tggtcatact ttgcagcaac cttaagagga ttttaaaatt   9060
tatattacta ctactattag gttatagttg atttcattaa ttccttcttc aataccttat   9120
ttaactgttt taccacttgt ctagtgaaac aagtacctct gtcactggag agttctccag   9180
gaatgcccag taaggaaata cattttctaa taacctttta tctacggtta tggcattgat   9240
tgatctttgt gcatagaaat gctttaatac aaccagaaaa catgcaatga agctggcagt   9300
tgaattaact ccagcttcaa gtgttcaaat gatctaccaa gtgccagaaa tatatcacct   9360
gaggtttttg ttgtcttact agaattatgg atttgataaa ccaaatatta gttataaacc   9420
atttagtaat cttagaatag tcacctcatc aatatttttt cactgtttgg atcattttct   9480
ctcttctatg atgagtcatg gaatacggag cttttagtaa tggaaatttt aagaactcag   9540
gaaggaccag gcggccatct agggtctcca tgagtgcatg cttcacattg gaattacaga   9600
ctctaaagta caaattttaa tacaatgagt tgcaatttat gcttctctaa ttcaggtaca   9660
taacactggt ttattaaata ggttatcata ggtaatttga tggtgccatt gcactccagc   9720
ctgggtaaca gattgagacc ctgtctctga attggaactg cacgggggca ctgtccttgg   9780
aggggtgaat gggcatgaag aggtgtctgg gtatgagcca caggtataga atttcactct   9840
tctctgccat cctctgttac atcctgggta cctgcctgcc actgaaagaa tgaggtaaaa   9900
gaggtggtgg cacgaatcaa atagatcttg ctgtgccaat gagagagagc agactagccc   9960
atgtcagtgc caggagagtg gaggagagag ggagagcagg agaggagtgt gggtagggag  10020
tgctcatcaa cagtacacat agtgccctat accggtaact gccactggct cagtatttac  10080
```

-continued

```
ctgggttatc actgcttacc atgcctgatt ttatgattaa ttatctactt atcattacta  10140
atccatcaac ccactttcca atgggagaat tagaacactg acaatacctt ccagctcctc  10200
ttccccttcc ccctcccatg ttgaccatac tcctgaatct taggctcgtt atccttttac  10260
tattaataga gttatttttt taatttctga tcaatggtct ttttaatgat accaagtaca  10320
gagtatatat gccaatacta ctatgaattt ttaaattatt tgctcagaca gaatacatgg  10380
acatacaaat gatgaatgtg ataattgtca tacatatata tttatcttag acacttagtc  10440
aaaacatgtg gtctttggtt atcagttaga cactgtcact ttacctggaa gatacaaggt  10500
aattggtcac agactctcaa attatgaaac atttagattt ttcaggggaa tgacatggag  10560
ggagccaagg agtcttatga ttagataaga tgttgtttgg gtggctcacg acaccactgg  10620
gcaacactca aagaggtggt ggcttatacc tgtaatccca acactttggg aggctgaggt  10680
gggaggatcg cttgaagcca ggagttagaa accagcctgg gcaaccaaac aagacctggc  10740
tctacaaaaa agttttaaaa atttagccag gcatggtggc atgtgcctgt agtcccagct  10800
acttgggaga ctgaggcagg aggatgactt gagccttgta gtttgaggct gcagtgagct  10860
atgatcacgt cactgccctc cagcctgggc acagagcaag accctgtctc ttaaaaaaaa  10920
atcatctgca atgtgaggag tgataacatt taggaacgtg tgtataggtt taaatgctgg  10980
tcaaagacat cctacacaat tcgctgaacc ttctctctaa gggttttttc ccaagctctg  11040
cagacgctat ctgggcacaa atcatgcctc tgttaacaga atttgctgtt ccttctagct  11100
cttggtatcc cactgcccgc tttctttatg aaagctggta tggtcattga atatcccaat  11160
cctttacaaa tttggaaaca agcaaaactg tcaatgaaat ttgtatttgc ctaaaatgag  11220
ttttctttct ttcttttta ttattattat actttaagtt ttagggtaca tgtgcacatt  11280
gtgcaggtta gttacatacg tatacatgtg ccatgctggt gcgctgcacc cactaactcg  11340
tcatctagca ttaggtatat ctcccaatgc tatccctccc ccctccccc accccacaac  11400
agtccccaga gtgtgatgtt tcccttcctg tgtccatgtg atctcattgt tcaattccca  11460
cctatgagtg agaatatgtg gtgtttggtt tttttgttct tgcgatagtt tactgagaat  11520
gatgatttcc aatttcatcc atgtccctac aaaggacatg aactcatcat tttttatggc  11580
tgcatagtat tccatggtgt atatgtgcca cattttctta atccagtcta tcattgttgg  11640
acatttgggt tggttccaag tctttgctat tgtgaataat gccgcaataa acatacatgt  11700
gcatgtgtct ttatagcagc atgatttata gtcctttggg tatataccca gtaatgggat  11760
ggctgggtca aatggtattt ctagttctag atccctgagg aatcgccaca ctgacttcca  11820
caatggttga actagtttac agtcccacca acagtgtaaa agtgttccta tttctccaca  11880
tcttctccag cacctgttgt ttcctgactt tttaatgatt gccattctaa ctggtgtgag  11940
atggtatctc attgtggttt tgatttgcat ttctctgatg gccattgatg ttgagcattt  12000
tttcatgtgt tttttggctg cataaatgtc ttcttttgaa aagtgtctgt tcatgtcttt  12060
cgcccacttt ttgatggggt tgttttttc ttgtaaattt gtttgagttc attgtagatt  12120
ctggatatta gccctttgtc agatgagtag gttgcgaaaa ttttctccca ttttgtaggt  12180
tgcctgttca ctctgatggt agtttctttt gctgtgcaga agctctttag tttaattaga  12240
tcccatttgt caattttgtc ttttgttgcc attggttttg gtttttaga catgaagtcc  12300
ttgcccatgc ctatgtcctg aatggtaatg cctaggtttt cttctagggt ttttatggtt  12360
ttaggtctaa cgtttaagtc tttaatccat cttgaattga ttttgtatac taaaatgagt  12420
```

-continued

```
tttcaaaagg atctttgtgg ctaccttatt agttcataga aagtggaggc ttgtctggaa  12480
tgatattaaa gaattttttt cattttaatt gttttagaga cagggtctca gtctgttacc  12540
caggctggag tacaatggca cagtcatagc tcactgcagc cttgaactcc tgtgctcagg  12600
agattctccc accttagcct ccagagtagc tgggactaaa agtgtgagcc accatgcccc  12660
actatttatt tttgtagaga tgtgtttggg ggacggtctc actatgttgc ctaggctggt  12720
ctcgaactcc tggactcaag caatcctcct gcctcaacct cccaaagcat tgggataagt  12780
tttgcataga catgtttgac cctctccctt cctttattgc agcaaagatt tccattttct  12840
cacagggagg acttggggca aattgttttt gtcgttgtta ttgttatttg aggatgtggg  12900
tgggtcatct tggttaatgt cagtgcaaga acggtgtctg ctcctcatta ttggggttcc  12960
ttagctattc aggcaggcag cagctccctt gagaagactt cctgaccccc aggtccccat  13020
catatgctct catacaccag ctgcccctcc ttactgagcc tatgtccttg atagtgctgc  13080
atttacctgt gatcctgtgg ctgagctctc cctcacactt ccagacaagg aaggcctgtg  13140
aggtatcagc acagtgctga acatagtacc tggtacacaa taggcattta gtaaatatgt  13200
gaacaggaac aaatgaagga gtcagtgagt gaaagctcca agcctgactc agcggaactg  13260
gcagtcggcc agggcctaca aagtgctgcc tggccctcag taggggggtgg cagatctggg  13320
gatccctctt caccaaatag agttgcatca tacaggtaaa ggtcccaagt gcctattgtt  13380
ttcttttcat cattttccat gtgtgacaag agtatcacgc aatcatgtga atcaatggac  13440
ttagttttct cactagacta atgtgtctag gaattatctg tgttgtcatg gggattttcc  13500
aggtgtcatt tacaactacc tgtggacaag atgaggtgct accctcatct tagaattagg  13560
gatggtggct gggcatggca gcccatgcct ataatctcag cactttggga ggctgaagca  13620
ggtggatcaa ctgaggtcgg gagttcgaga ccaacctgac caacatggag aaaccctgtc  13680
tgtactaaaa aacacaaaac tagctgggca tggtggcaca tgtctgtaat cccagctact  13740
cgggaggctg aggcaggaga attgcttgaa cccaggaggc ggagtttgcc ctgagctgag  13800
attgcatcat tgcactccat catgggcaac aaaagtgaaa ctccatctca aaaaaaaccc  13860
aaacagaaac aaacaaacaa acaaaattag tgatagtgat gctcagcctg gggaaagcat  13920
ttgtccagtg gcacacaact gggaaaaggg gaagctgaga tccagcagga ggtctgtctc  13980
caaagccctc ctagactaaa gctgcttaac aatttgtgga ttatgaaatt ctcatagagt  14040
ttgattaaag ctgtggcccc ctcttttcca aataggcaca tacatgtttg cataaagttg  14100
tgaggcttca cacactccct aaaactcttt cataaacctt ccaaggatcc tctaggtatt  14160
cacgaccatc tattatgatt gcatctcttg ggggtggggt aaagagggag ggcatgagca  14220
agtgtgcatc agggctgagg aaggtggcgc tgttgcttct ccatttccca ataagcttcc  14280
agattctttt tgatgtcaga gggatgtggg ctcgtgtctc agattcaacc cgtatgcatt  14340
gagtcacagt tttctcttcc gtcagttaag atcatgacaa tgagaatgtg tgcccctaag  14400
gtggttgtga ggattaaatg ggatattgca tacagctagt atataataag tgctcattaa  14460
atggcaacta ccttgatcca ctcattcatt tattcacgaa tccaataaca attcactggg  14520
cactttctat gtaccaggaa atagtctagg aattgatgat gtggcatctt ggacaagaca  14580
tacgaggtca ctgcgcttat ggacattcca ttggcagaga cagataagca aaaaataaac  14640
agataaggaa atgttaggtg gagaagagct acaattaaac taaagcaggg ggatatttca  14700
gacagtgatg agaactacgt tagattgagt ggttagggga agactgtctt gttttttttt  14760
ctgagcagag acaatgaaag attcaggtgg aaggcactag aaggaggcag ggtggctac  14820
```

```
aagaatcctg aaacaggaaa aatgtcagag aacaacatgg aggaatgagt gggaggagaa  14880
gtcagagcgg taatagggcc acgtcatgta ggaccatgtg aaccctcagt ggagacttca  14940
gatcttattc tcagcaaagt gggaatattg taggccttgg tgagcacgtg gatattaatt  15000
attttacatt ttagtggggt taccctggct tgtggggcag tgaaacaatt gttaagtgga  15060
gtaagcatgt catccagaag tccagtgaag ggctttgca gagatcaatg cagggcattt  15120
gtaagtaaac ttaacaaatt ttatgacttt tatgtcaagt ttttattgaa cttgaacatc  15180
actgtaaaaa gcgcacagct caatgaattt tcacaaactg aacatactca tgtaattgac  15240
atgcaggcca agtagcaaga atgccccgaa accctgcacc ctgttctttt ctattcacta  15300
tccacctacc atcttgatca tgggttgatt ttatctgtgt atgaacttct tttttgtttt  15360
tgtttgtttg ttcctgagat tgaattttgc tctgtcgccc aggctggagt gcagtggcac  15420
tatctcgcct cactgcaacc tccgcctccc cgggctcaag caattctctc gtctcagcct  15480
cccgagtagc tgggactaca ggtgagagcc accatgcctg gctaattttt gtatttttag  15540
tagagatggg ttttcaccat gttggtcagg ctggactcaa actcctgacc tcgtgatcag  15600
cctgcctcag cctcccaaat tgctgggatt acagatgtga gtcaccacgc ctggccctgt  15660
gtttgaactt catacacata aaattatgat gcattgactc ttttgtgcct agttgcttcc  15720
actcaacatt atgcctgtga gtttcagcca cgttgtcgcc tgtagctgtg gtttgttctt  15780
ttttgttgct gtatactagt ctattgtgag aaccctcact gattgtctat atctatattg  15840
atgagcattt tattaagaaa gcttctgtga atattttgtt catttttttgg tgaacacaca  15900
tacacatttt tgctgggcat gtacctggga gtgaagtggc tggtttcctg ggtatccatt  15960
tgttcagctt caggaaatac tgcccagcag ttccccaagt ggctgcacag taatcccacc  16020
ttatccactg gagatatctt ctgagacccc cagtggatgc ctgaaacccc acataatact  16080
gagcactatg catactcttt ttttttccta tacaatcaca ttatataggg agggtggtat  16140
acacagtgca gacatggtgg acaaaggatg attcgtgtcc ggggtgggac agagtggatg  16200
gtgagagata tcatcatcct actcagaatg atgcacaact taaaacttac gaattcttta  16260
tttctggaat tttccattta atattttcag actgcgatta gctgcaggta actgaaactg  16320
caaaaagcaa aaccacagat cataagaagt atgcggtggg ggtgatattc atcgtatttt  16380
atcaaccatc tttactgttt agggcacaag ccaatcagag cagaccctgg ctgggccacc  16440
cattaaccta agcttgtcca acctgcctta ttttgttgtt gttctgtttt gttttgtttt  16500
agctttttag cagcctgaag ccatggtttt cagtttctgt ctccagtgat acacagaaag  16560
gaaggatgag gaaggggctt tactggccca accagaaacg gaaactaaga acccatgact  16620
gtattctctc ccttggacag cgttaaccat taacccttaa ttgctgggtc ccagcagggg  16680
aaagggcagc ctggggaggc ggatgttggg gaggggctaa ttaccaatct ggtatgtaag  16740
tattttgata gttttacaaa tgaggtgtat gctgactaac agccacccct ggtgtggatg  16800
tgattggcag ttccgagaga aatatgggga cgtcttcacg gtacacctgg gaccgaggcc  16860
cgtggtcatg ctgtgtggag tagaggccat acgggaggcc cttgtggaca aggctgaggc  16920
cttctctggc cggggaaaaa tcgccatggt cgacccattc ttccggggat atggtgagag  16980
cctcagaggc actgggaggg ggcgggtggg gggtgcatca gggaagggag tatatgggag  17040
gaagaaggac tcagagcctt cttccaactt cttctacaac caacccacac ctcccctgca  17100
ccccaggtgt gatctttgcc aatggaaacc gctggaaggt gcttcggcga ttctctgtga  17160
```

-continued

```
ccactatgag ggacttcggg atgggaaagc ggagtgtgga ggagcggatt caggaggagg  17220
ctcagtgtct gatagaggag cttcggaaat ccaagggtga gtcctggggg atgaatagga  17280
aagaaagaca atgaaacact gagagatgca ggtgcacggg aatagaaaga cagagaggta  17340
tataagggca cagacagaga cagacgaaac tggagacacc atcagacaga gggatagaga  17400
cagagaggga gagagacagg ggaatagaga gggatgggga tgggcaggag agaaacacag  17460
agagccaggg aaagagagag atgccaggtg tataatgtcc aagagttact caaagaggct  17520
ggatgtgatg actctcacct gtaatcccag tactttggga agctcaggca ggaggattgc  17580
ttgaggccaa gagttggaga acagcctggg caacataatg agatcctgtc tctacacaat  17640
atagaaaaga agtgagccac gcatggtggt gtgtgcctgt agtcccagct actcaggagg  17700
ctaaggtggg actacaggat cacttgagcc caggaggttg aggttgcagt gagctgtgat  17760
tgtaccactg cactccagcc tggacaacag agcaagatcc tgtctcaaac aaacaaacaa  17820
accctcaaag acatataatt tcatggatca attgtgtctg tcaaagtcaa aaacggaagt  17880
taagtaaaag aaaaaaacta cagacattta acaaataatg aactgtgttt tccttgccct  17940
gggtgaagtg ctgatgagct ggcagtgagc agacaggcca ggtggggtgt tctgcccggg  18000
tgcagctgga ggggtcatca aagaatcact aggttatttt tgagttctcc ataacttggt  18060
gtctgtgaga catgtaggtg aagggtctct ggctagcacc tccatctcat tcatgccagg  18120
tgtttaccat ctctcttatc aaaatttctc aagagactct gggatgtaaa tgcagaggct  18180
gcatggggag gtagagaccc aggagctata gggaaacggg gacaagaaga ctgaagagaa  18240
ggacaggaag aaacagtgac acaggcagga ggaaagagac agatggaggg accaaaacaa  18300
aaaaatatag gttgggtatg gggctcatgc ctgtaatccc agcactttgg gaggctgagg  18360
ctggcggatc atttgaggcc agcagttcaa aaccagcctg gccaacatgg tgaaacccca  18420
tctgtgctaa aaatacaaaa attagccagg cttggtagca cgtgccttta atcccagcta  18480
ctcaggaggc tgagacagga gaattgattg agcctgggaa atggaggttg ccgtgagcta  18540
agatcacact actgcactcc agtctgcatg atagagtgag actctgtctc caaaaataat  18600
aataataata ataaaataaa gaacggcagg ggggagacaa atatacacac agagagacag  18660
aaagaaacaa aggcaaagag aaattgaggc agagaaaatt agagagacag acagacaaag  18720
cttaggaaaa ggtctgcaga ggaatgagag aagacaggca agtgagaacc agagagaggc  18780
tgcactaacc tgatgttctt gggtccttac agaccactct ccctccagct ggggccagtg  18840
ctgagcctgg tgtatacagg tatcacttaa caagtacaga ataattccca gaagactgga  18900
gagccctaga tgtggaaaga agagattaag ggggagtaat aggtaggggt ggaaagatgg  18960
ttttttattt gttttaaatt agagacgggg tctcactctg tacccaggct ggagtgcagt  19020
ggcacgatca tagctcactg cagcctcaaa ctcctgggcc catgtgatcc tcccacttca  19080
gcccctggac tatttcaact gggactacag gcatgtgcca ccatgtctag ctacattttt  19140
tttttttttt ttttgtagag acagggtctc cttatgttgc ccaggctggt cttgaattcc  19200
tgatcctttt gaatcaggct cccgaagtgc tgggtttaga ggtatgggcc cctgtgccca  19260
cccagggctt tttaatttat ataagcaatt gattgaacac ctactctgcc cagcccctat  19320
ccctgggatt taactgtact cactcccaga gtcagaggtg gggcctgaga ggaggtgcag  19380
agtgagaacc ggctgcatgg actctatagc tgtgttgcct gggtctaaat cctggcctca  19440
gtaatgagta gctgtgcaac tttggtcaaa ttactcagcc tctcggtctg cccatctata  19500
aactggagct aataatcaaa ttgcatctgc ctcacattgt tgtagtgaga gttcaatgga  19560
```

-continued

```
attacgcgtg acgtgctggt acataattag ctgttacggt tattctcatg tttaccatta  19620
ctgagtgatg gcagacaatc acacagagat aggtgacagc ctgatgttcc ccaggcactt  19680
cagtctgtgt ccttgacctg ctgcttcttc ctaggggccc tcatggaccc caccttcctc  19740
ttccagtcca ttaccgccaa catcatctgc tccatcgtct ttggaaaacg attccactac  19800
caagatcaag agttcctgaa gatgctgaac ttgttctacc agactttttc actcatcagc  19860
tctgtattcg gccaggtcag ggagacggag agggacaggg ggtgtggggg tgaggtgaac  19920
acccagaaca cacgagaaaa ggatgacctg tcttgggggc tcagaaatgc agcttatcct  19980
tggaagaaac gcagacatgt gaagaatcag ggacatggag acctggaggg aggagagacg  20040
gtgagacagg gatagagaca ctgagagaga gaatgaggcg tgatggggag gcagaaatag  20100
agtcagagag agactgagag aaggaagatg agcaaaaaca agacaaagaa gagcagaaat  20160
caagagattc tgagagacag agttgatgag aatgagtgtg aaagagaggg agagagagag  20220
aacgaataag gctttgggct tcatgtctat tctgctcctg gatgtcattt ctgttttatt  20280
tttttagac ggagtctcgc tgtttcattc cagctggggt gtagtgttgc catcttggct  20340
tactgcaacc tccacctccc gggttcaagt gattctcctg cctcagcctc ccaagtagct  20400
gggactgcag gcatgtgcca ccacacctgg ctaatttttt ttttttctt ttcgagacag  20460
agcctcgctc tgttgcctag gctggagtgc agtggcacaa tctcagctca ctgcaacttc  20520
cacctccctg gttcaagcaa ttcccctgcc tcagcctcct gtagctggga ttacaggcgc  20580
ctgccgctat gccaggctaa tgtttttgta tttttagtag agacggggtt tcgccatgtt  20640
ggccaggctg gtctctaact cctgacctca agtgatctgc ccgcctcaga ctcctaaagt  20700
gctggaatta caggtgtgag ccaccatgcc cagactgctt ctggttcttc tgtatccttg  20760
cttctcagtc tttggtaaag ctctccacct aaagaaaatg aaggataaat gacaataagg  20820
aacagcattt cttcattttc tcccatttct ccttctccct ctgtgttttt tttttaact  20880
ttccccagat tgtaaaggca gtcttctgct cttttaaaac aaaatactaa aatgtctcct  20940
tatttattaa cctggaaata tgcctattac atattaaatt taagaatatc aagctgcaga  21000
acagtatgca tagctgtagt ttgttgttgt tgttgttttc agacagtatc ttgctctgtt  21060
actcaggctg gagtgcagta gtgtgatctc aactccctgc cacctccacc tcccaggttc  21120
aagcaattct catggctcag cctcccgagc agccgggact ataggcgagc gccaccacac  21180
ccagctaatt tttttgtatt tttagtagag atggtgtttc accatgtcgg ccaggctggt  21240
caacatagct acagctatta agcagggatg tatgttggat tcacatgtgg ggttgtcaca  21300
gttatggatt ttcaggaccc tactttctgg gcggtctgat ctggaaagtc tgggatgggg  21360
cccaaggtga gtacttgtaa caagcccgac cagtaattct aatgttctcc tcccaccgag  21420
aaccacagag aaaagtctgg aaggagaccc accagacagt taacaatggt tatctctaga  21480
aggagagatt aagaaggaaa tttacatctg actatatatg tttgcatttt tgcaattatt  21540
tgcaataaat taggcattcc attcttcatc aaagtaatag aaataacctc caaaatacgt  21600
agtcctaaca tgtcagcagg cttatcttgt gtaagaatca ttttattaat atctgacaca  21660
gcaagggaga tgaggagagg tgggaagagg gagagaaaag tatgagaaag acaaataaac  21720
aggctgaggt agacaatggg tgacacagaa aggaagtgag acagagacta agagagatag  21780
aaaggagaga ggcagggaga tggggcagag gccaagaaaa agacagaagg atgagggagg  21840
aagatgcaga aagaggtaaa tgtgagatag atcaaaggag atatagagtc agtgagtgag  21900
```

-continued

```
gggttcagag gcagaggggga gtggggaagt ggggttccca tggagggatt ggggcccagg  21960
aggcgctctc tccctgtgac ctgctagctc agccctaggc aaacctcacc accccttctt  22020
tcttgcagct gtttgagctc ttctctggct tcttgaaata ctttcctggg gcacacaggc  22080
aagtttacaa aaacctgcag gaaatcaatg cttacattgg ccacagtgtg gagaagcacc  22140
gtgaaaccct ggaccccagc gcccccaagg acctcatcga cacctacctg ctccacatgg  22200
aaaaagtggg gtctgggaga ggaaaaaggg aagggagggg agggagggca agatggagag  22260
gtgagaagag ggagggaaaa ggggtaggga aggggaagat ggggagggaa gaagaaagac  22320
tagggagggg agaataggga aagggaggag agaacatgag gaaggaaaga aagatgaggt  22380
gaaaggaggg agaaaatagg gaggaggaac tgagacaggg agagagggga ggtgggaaga  22440
cagaatgaaa gacagaggga gagagagaga agactggctg aggaaggaat tcggggcaag  22500
ggacaaaaat acagcaacaa gagaaaaaac tcacagaggc agaaagagac ggggacaaaa  22560
agagagaaac acatcaaaga gatgtggaga gagatagaaa cagagttagg aagactaaag  22620
agaggctgag agagatgagt tagagatacg cggttggatg tgtagaggac agagaaaagc  22680
aaactgggcc agatagtgtc aaagaccttt aggccaacgg agggcagcca gggagatggg  22740
cgtatacaca gcaaggctac agcctcccct gaccctcccc ttccttccct actgtggacg  22800
caggagaaat ccaacgcaca cagtgaattc agccaccaga acctcaacct caacacgctc  22860
tcgctcttct ttgctggcac tgagaccacc agcaccactc tccgctacgg cttcctgctc  22920
atgctcaaat accctcatgt tgcaggtggg ccagggacag ccagtcaagg gggtcttctg  22980
acctccttct gagctgcaga aatggggcta tgggtaccac ctggatgaga gaggggatgc  23040
tggcttccta ttctgggagc actgtaggct ctgggctaga ttccaaccaa gccaattctg  23100
ttggtggatg catggatgca tgaagaatct gtccatgcgt tctcccactg ttttcttcca  23160
tcacttaagg attttttgtt ctaaggtttt tgtttgtttg tttgtttttt gtttttttggt  23220
tttttttttt ttgtcttttt tgagacagag tctcgctctg tcacccaggc tggagtgcag  23280
tggcatgctc ttggcttact gcaagcttca cttccagggt tcacgccatt ctcctgcctc  23340
agcttcccga gtagctggaa ctacaggcgc ctgccaccac acccggctaa tttttttgtgt  23400
ttttagtaga gatggggttt aaccatgtta gccaggatgg tctcgatctc ctgacctcat  23460
gatgtacaaa tttagggggt acatatgcag ttttgttaca tgcgtaggtt ttgtaatggt  23520
caagtttggg ctgttagggt atttatcacc caaacagtgt acattgtacc cattaagtaa  23580
tttctcatca ttcacccccc ttctgctccc tcactcttct gagtcttcac tgtgtatcat  23640
tcctctctct gtgtccatgt gtacacattt tgtagcactc actcatgagt gagaacatgc  23700
aatatttgac tttctgtgcc atcacttaaa aatcgatcca tccacttatc atttcatcta  23760
ttcattcttt aattcattaa ttaaagaatg tataattact gattctttca tttatgattc  23820
atctaaggac atatactgtc attcatttat ttggattact tgatccacaa gttgatcctt  23880
tgaaacagtg gtatgttgat ggactatttg tcattgattc attggctcat tcattcattc  23940
attcatgcat tcatccatcc ttctacgaac taggtttcac tcttatcctt ccatgagtca  24000
acctttcaat tcacccttaa tccatccgtg atttccttca tttatcacaa taattcactc  24060
atttattcac ctctgatcta cttatcattc aatccagcct ttcatttact cctttattta  24120
ctcatacttc actaatttaa ttattcactt gctcttccat aaatctagcc attcatgtga  24180
ttattcatta attgggttca ttgatttctt tgtctatgga tcattcatta gtgattaatt  24240
aatcaatcca tctattaatt gataagtaaa tacagacatc catttattgg tttgttcatt  24300
```

-continued

```
tattcatcaa tctttccatc catgaattga tctattgatt gattgattga tgtttttatc  24360
cagttgttca tgaattcatc tattgttcta ttacactgtt atatacctga ggaccaagaa  24420
tagtgtctca actatattat aaacacaata aatattagtt cattttctac tcatcttaga  24480
gagggtgttt tgagaggttt gtagcctgga gttcttaatc tgaaattcca tgcaaaatcg  24540
tggtgtgtgt gtgcatgtgt gtgtgtgtac ctgggcatgt gggaagagga tctgtaatat  24600
tcattagatt tcaagcagtg agaattcttg ttgcttcctc cctcctcccc tcaccccatg  24660
ctgattactt tgaggggtat caaggatcta accctttact ataggttttt cattggtcaa  24720
tagaaagtag tgtccttgct gaaaggtctc tttttaaaaa aatttttttt tcttttgaga  24780
tggagtcttg ctctgtcacc cagtctagag tgcagtggca tgatctcggc tcactgcaac  24840
ctccacctcc tgggttcaag tgattctcct gcctcagcct cctgagtagc taggaataca  24900
ggtgtgcacc agcacaccca gctaattttt tgtattttta ggagagacgg gattttgcca  24960
tgttggccag gctcatcttg aactcctgac ctcaaggaat ccacccacct caacctccaa  25020
aattgctggg attacaggca tgagccacca tgcctggcct gaaatgcctc tttaaaatga  25080
gattcattgg tcttcttttc tgtacagaga gagtctacag ggagattgaa caggtgattg  25140
gcccacatcg ccctccagag cttcatgacc gagccaaaat gccatacaca gaggcagtca  25200
tctatgagat tcagagattt tccgaccttc tccccatggg tgtgccccac attgtcaccc  25260
aacacaccag cttccgaggg tacatcatcc ccaaggtaag accggctgga accccatagc  25320
cctcctgttt gggcatcctg gattctctta atccccgaac tcaacctttt gttagctcct  25380
taattgagtc ccgttgtttt tgtttttttgt atttcttttt tgtggagtgt gtggagggtt  25440
ggagggaatg gcaatatctt ttgatcttgt gatcctccct caggacacag aagtatttct  25500
catcctgagc actgctctcc atgacccaca ctactttgaa aaaccagacg ccttcaatcc  25560
tgaccacttt ctggatgcca atggggcact gaaaaagact gaagctttta tccccttctc  25620
cttaggtaag ctggacccac aatttctttc ccagacacca gagggcaggt actatcccca  25680
acttgagaaa aacaacgaga gatactgatt atttgagcac ttaatatatt ctgattgctt  25740
cacctgcctt atcccattcc atcttcacta caaccctata aggaggcttg agaaagaaga  25800
ttacattccc aaaggcacat cttggcaagc aggaccttgg gcaagtattt taacatctct  25860
aaacctcagt gagttcattt tcttaaaaag aaaaaatctg ttgggcacca ctgtaagccc  25920
agtgctgtac tgggggctga agataatgca tcaaacaagt cacacagaga cagggttcct  25980
gccccaggaa atttaaagtc cagcagggaa gatgggcatt catcaaataa taataaaata  26040
atcatctcat gaaatgaatg aatgcctgca acatgcttag aactgcctgg cacaaaggac  26100
atgctcacaa gggcaattat tattataatt agacataatt gtgataagtg ctctaaaggg  26160
agctttggga gcacaaaata ggaaatagta gctaatcttg tggtgggtcc gtaaggaaaa  26220
gcttaccaga ggaactggct tccaagctaa catgttcatg ggtgagcatc aatcaaccat  26280
tgcaaagtgt gttccaggca aaggaaacag caaggacaaa ggccaaaggt agaaacgtga  26340
tatggcacca ttgagaacct ataggaagtc cagtgagcct tgggtgtaga ttgcagaagg  26400
aaataagaca aagggctcat ctgggcagga ccttgaaggt tgcaggagga gtttggattt  26460
atggtctagc actgggaagg tggaaaaggt cttgacgtgc tctgacttgt cccagttctc  26520
atcctctact ctttggctgg ttaaaagaaa aactttagac aaattaaact tagcagagtc  26580
tatctgaaca aagaaacaat tcatgaattg ggcagcacaa ggaaccagta aaggttcaga  26640
```

-continued

```
gagctccatc cagcaatgtg gtcaggcact atttatccac agggaaagga actgaggtac  26700
tgaaacagcc tgattggtta cagctctgtg tttgccttat ctgagcatgt ctgggcagct  26760
tgtagcctgt gactggctga agcttggctg ccctgattgt ccaaggttac ttgttacaag  26820
aatatactct caagtttgtt tacatgttga gttacattac aatttgttat gtagggaggc  26880
tgctttaggc caaatttaat tgaatttaac atgcaccatc catgaaaggc cccagaaaca  26940
aacccccagt cttgagtttc atcagtgact tcagtgatcc agggtttggc ccagcccccg  27000
gttttgcgca gtacagtgac ctccttccac attttatctt caatgaaaat tgggaacatg  27060
tgtggtgatg gcttgaatgt caatgtcttc tctcaatttt gctatctgaa gtttcttttt  27120
tttttttgt cttcagacgg agtcttcctg tgttgcccag gctggagtgc agtgtcacga  27180
tcacagctca ctgcaacctc tgcctcccag gttcaagtga ttctcctgcc tcagcctccc  27240
gagtacctga aactacgggc gcatgccacc atgcctggct attttttttt atttttagta  27300
gagactgggt ttcaccgtgt tagccaggat ggtgctgatc ttctgacctt gtgatatgcc  27360
cacctcagtt tctgaaagtc ctgggattac aggcataagc cactgcgact ggcctgctaa  27420
tttgttttaa gagaggcaga gatgtaggga aataaggaca gagacagata agtaacaaag  27480
ataatgagac tgagaaacag agttagggac aaagagggaa cacatagaga tagagatggg  27540
gagccagtgg cagaaagaca gagggcaaac ctcagacagt atacagagag gaagagagag  27600
agacacagag agagagagag tcacgtaagg agaaggagga ggaggaggaa taagaggaga  27660
gagagtagga aaaggaagga ggaggggaga aaggagggaa aggagagaaa cagaataaga  27720
gataggaaaa agagagagtg acataaaaag agaggaagaa agaatgaaca agacaaataa  27780
ggtatcttta gagggagatg aaaagaaaga atgagagaga aagagattgg ggagaaatca  27840
gattcaaata gatggagata ggaagttaag caagatggaa gaaagccaaa aaaaggagag  27900
gaaaagaaga aaagctgtgt ctgacaggta tagacagaga aaaagacagg agtagggctg  27960
ccaggggcag aaagaaaggt ataacccaag ccaaaagggt actgcagcca aagaaattcg  28020
aaaggtgtcc aaacagacgg ccccagagat ggggagggcg tgatgagagg gagataataa  28080
gcctcaggct gttgtgaaaa atgttaggtc acacaaagag ttacagaaga acaggcccag  28140
agacctgcct gtttctaagc tcatgtcacc caccttctgg gtatgccaaa gggatgtgga  28200
cacttttcca aacacctcca catagacaca cttgtccaac aacttgacag gcatagggaa  28260
tgcctgaaaa ctcacacttg acatggcctt tccaaggttt gcagattatg aaacactgaa  28320
gtgaagggaa aggctccctt tgtctctgcc tgagcttttt ccagcaccct ttgttcttat  28380
ttttctccca atctgtggtt tagaatctac tgggggttcc ttgcacctct gagaatcagt  28440
ggaagccata gaccctccct gtctcatacg catcagtccc attcacaatt tatatacaat  28500
tgggcttttc ccccttgag ctcttgaagc ctgtggatct caggctgaga ctagaagaca  28560
gcctagagac acagacacag acacatggcc agaaacacat accccacaca taccccagaa  28620
acaaacacaa ggcagtaacc aaaccttaag cctccttagc acaagccaag tgctattcta  28680
agaattttta caattgtctc ctttaacctc acaagagccc tttgagggag gtgccattct  28740
ccccatatga gaagtgaaga acactaagaa tgttgtcata aatgtgctca cactcacaca  28800
tgtacaggta cacacacaca cacacacaca cagaaccaga aatgggtcat tatactctgt  28860
gggtttcacc aacccttttgg aactgtaaca gaagctagaa actctcttat ataaaaatga  28920
acatggcgcc gggtgcagtg gctcatgcct gtaatcccac tttgggaggc caaggcaggt  28980
ggattatctg aggtcaggag ctcgaggcta gcctggccaa tatgatgata ccccatgtct  29040
```

-continued

```
actaaaaata gaagaaatta gccaggcgtg gtggcaggtg cctgtaatcc cagctacttg  29100
gtaggctgag gcacaagaat catttgaacc acctgggagg tggaggttgc agtgagccaa  29160
gatggtgcca ctgtgctcca gtctgggtga caaagagaga ctccatctca aaaaaaaaaa  29220
aaaaaaaaaa aaaaaaaaaa aaaagagaga gagagaaatg aacgtggcac atccactcaa  29280
agatttgcat ctggtttcag agcagcttcc taaaagtcca ccctgaattg taggttaaag  29340
gccagtctta tgcaaatctg ttgcagtgga catttgtgtc tgggcttagg gacatggcag  29400
agcgaagtgt atgcacctgc cctgtgccca cactggtgac cttctgtgtc cacagggaag  29460
cggatttgtc ttggtgaagg catcgcccgt gcggaattgt tcctcttctt caccaccatc  29520
ctccagaact tctccatggc cagccccgtg gccccagaag acatcgatct gacaccccag  29580
gagtgtggtg tgggcaaaat acccccaaca taccagatcc gcttcctgcc ccgctgaagg  29640
ggctgaggga agggggtcaa aggattccag ggtcattcag tgtccccgcc tctgtagaca  29700
atggctctga ctccccgcaa cttcctgcct ctgagagacc tgctacaagc cagcttcctt  29760
cccctccatg gcaccagttg tctgaggtca cattgcaagt gagtgcagga gtgagattat  29820
cgaaaattat aatatacaaa atcatatata tatatatgtt cttgtttttt gagacagagt  29880
ctcacactgt tgcccaggct ggagtgcagt ggcgtgatct cggctcactg caacctccac  29940
ccccggggat caagcaactc tcctgcctca gcctccctag tagctgggat tacaggcatg  30000
cactaccacg cttggctaat ttttgtattt ttagtagaga tggggtttca ctgtgtaggc  30060
caggctggtc tcgaactcct gaactcaagt gattcaccca ccttagcctc ccaaagtgct  30120
gggattacag gcgtgagtca ccgtgcccag ccatgtatat atataatttt aaaaattaag  30180
ctgaaattca cataacataa aattagctgt tttaaagtgt aaaatttagt ggcgtgtggt  30240
tcattcacaa agctgtacaa ccaccaccat ctagttccaa acattttctt tttttctgag  30300
atggagtctc actctgtcac ccaggttcga gttcagtggt gccatctctg tccactgcaa  30360
cctccacatc ctgggttcaa gtgattctcc tgcctcagcc tctggaggag ctggtatcac  30420
aggcgtcccc caccacgcct ggctaaattt tgtattttta ggtggtcttg aactcctgat  30480
gtcaggtgat tctcctagct ccaaatgttt tcattatctc tcccccaaca aaacccatac  30540
ctatcaagct gtcactcccc ataccccatt ctctttttca tctcggcccc tgtcaatctg  30600
gtttttgtca ctatggactt accaattctg aatatttccc ataaacagaa tcatacaata  30660
tttgattttt tttttttttt tgaaactaag ccttgctctg tctcccaggc tggagtgcta  30720
tggtgcaatt tttgttcact gcaacctctg ccttccaaga tcaagagatt ctccagtctc  30780
agctcccaag tagctgggat tacaggcatg tactaccatg cctggctaat tttcttgtag  30840
ttttagtagg gacatgttgg ccaggctggt ggtgagctcc tggcctcagg tgatccaccc  30900
acctcagtgt tccaaagtgc tgatattaca ggcataatat gtgatctttt gtgtctggtt  30960
gctttcatgt tgaatgctat ttttgaggtt catgcctgtt gtagaccaca gtcacacact  31020
gctgtagtct tccccagtcc tcattcccag ctgcctcttc ctactgcttc cgtctatcaa  31080
aaagccccct tggcccaggt tccctgagct gtgggattct gcactggtgc tttggattcc  31140
ctgatatgtt ccttcaaatc tgctgagaat taaataaaca tctctaaagc ctgacctccc  31200
cacgtcaaga ggtgatctgt gccattttgt gtgtgattct tttattgtcg ggtctctagg  31260
gatttttctg gaaggaatgt tggtgagaat gcctctctca cctcaatgcc aactctgtga  31320
agggccaaac cattgtcttg ctcatccctg tactctcaac acagcgtgtg gcatatgaca  31380
```

-continued

```
ggtgttcaaa atatttggtg aggaatgaat gaatgagtgg ctaaatcagc cacccccctac  31440
ccccacagcc cacccaaaat ggagctaggc ctcctccatc agactatatc tcctccatat  31500
cccactttct tgtgaggtcc agaataaatt ctcatcccca aagggcccag gatgcccccca  31560
ttctgcctac cagttactct cgataccccg tgctgcaatg ccaccttttg ataaagctta  31620
gcgctattct tgcagtggaa ccactctaaa tccagcctcc aggctggacg cggtggctca  31680
tgcctataat cccagcactt tgggaggccg acgcgggtgg atcacttcaa gtcaggggtt  31740
cgagaccagc ctgaccaaca tacaaaaacc gtgtttcaac taaaaaagat acaacaatta  31800
cccgggcatg gtggtgtgca tctgtagtcc catctactcg ggaggctgag acagggtgat  31860
cgcttgaatg caggagggag aggttgcagt gagccaagtt cccgccactg cactccagcc  31920
tgggtgacaa agtgagactc cgtttcataa ataaataaat aaataaatcc agcctccaaa  31980
cattccacca gcaggaccac caccccttccc tgagggaggt gctgcaagtt taatatcatt  32040
atcacaagga tacatcagcc agcctgtggc cagtgggaag ctggccctgg gactccaccc  32100
tgagatgcta accttttggc gtctgcagca tctgccatct ttgggctcct tgtagcctct  32160
gaagagttaa cagagactct gccagtacaa atgcatggca cacattccct caccaaccac  32220
agaaataaca aacagagcaa catgtctttt aagagcgaca gcagaatgga aggcgggaag  32280
aatgaggacc acggtgccct cagccttctc actcctcatt gtccccagtg gcctcttgct  32340
actctggttc tggggccatc ccacctccca gggctgcctc tctcctaggc cctggcctct  32400
gcccttcctg gggggagcatt ttgcaaataa accacagggc tttctgaagt ctgtccaggt  32460
ggtgagatgg gagagtgtgg aagggatgga aaaggaggag gtgggtagac gggaaacagc  32520
tcacaggcag caaggcagtt ggggtcgtac tttgggtggg attccacaga caagcttggg  32580
aattcctttc tggcttatat attaactaca gaagcttctg gaattttata aggtgaaatg  32640
gagaggagac agactggagg gtgaaattct gatagacttg aggctttgag atgtggtcct  32700
ggggtggagc aagacaagaa aagtactgga gattggggtt tgaggagtct atgcaattat  32760
ttttattttt aaaaatcttt gtggctacat agcaggtgta tatatttatg tggtaagtga  32820
gatatttcga tacagacata caatgtataa tcacaggcat acaatgtaga caggcataaa  32880
gtgtatagtc acatataata ataacatcat ggtaaatggg gtaaccatca cctcaagcac  32940
tcatcatttc tttgtgttac attagagtta tattccctct gttatgctaa aatgtaccac  33000
aggctgggca cagtggttca tgcctataat cccagtattt tgggaggctg aggcagacag  33060
attgcctgag ctgaggagtt cgaaaccacc ctgggcaaca tggtgaaacc ctgtctctac  33120
aaaaatacaa aaaaaaatta gccaggcatg gtggcatgca tctgtaatcc cagctactct  33180
ggaggctgaa gcgggagaat tgcttgagcc tggtaggtgg agtttgcagt aagccaagat  33240
tgtgccactg cagtcccgct tgggtgacag agtgagactc catctcaaaa aaataaacaa  33300
gcaaacaaac aaaagtacaa tgaattattg ctgacggcca tcaccttatt gtgctatcaa  33360
aaactagatc ttattcattg tatcgaactc tattttttgta cccattagcc atccccagtc  33420
cctcacctcc acccttccca gtctctggta accatcattc tactctatct ccatgagtta  33480
aattgtcata atttttagct cccacgaatg agtgagaatg tgcaaagttt gcctttccgt  33540
gcctggctta tttcacctaa cataatgtcc tgcagttcca tccatgttgc tgcaaatagc  33600
aggatatcat tctttttttaa tggttgaata gtactccctt ctgtatgggc accatatgaa  33660
cacttaggtt gattccataa cttggctctt gcaaacagag ctgcaaaata cactggagtg  33720
cagatatctc ttcagtatac ggatttcctt ttttttgata tagatttagc ggtgggattg  33780
```

```
ctggattgtg tggtagctct atttttagtg gttttctttc tttttgtttg tttattttat  33840
ttctttattc attttttttg agatggagtc ttactctgtc acccaggctg gagtgcagtg  33900
gtatgatctc agctcactgc agcctccacc tcctgggttc aagcgattct cctgcctcag  33960
catcctgagt agctgggact acaggcacct gccgacacgc ttggatgatt tttgtaattt  34020
tagtagagat ggagtttcac cacgttggcc aggctggtct tgaactcctg acctcagatg  34080
actcgcccac ctcagcctcc caaagtgctg ggattacagg catgagccac cgcacctggc  34140
ctattctact tttttttttc tttttcttag ggaaactcca tgttgttcct caaagtggct  34200
ctattaattt acattaccac caacagtgta caagggttcc atggggatta cttcagattg  34260
agtggtcaga gagggctcct ttgagaagac ttctgagaat tggccatggg aaggtgtggg  34320
gagaagcctt ctcagctgag ggaacagcaa ggtcaaagac ccagaggtaa gaaagcaagc  34380
ttggaacctt ccaggagcaa caaggcattg gctctgataa tgccttctcc tgctaaaatg  34440
acagctctag gaaggcaggg ttcttatttc ctgtctatct atctatctat ctatctatct  34500
atctatctat ctatctatca tctatctatc tatcatatat ctatctatcc gtctgtcttt  34560
atttatttat agaggcagag tcttgctcta ttgtccattg tattagtcca ttttcatgct  34620
gctgataaag acataccgta gactgggtaa tttataaaga aaaaaagttt aataaactca  34680
cagttccaca tggctgcgga ggcctcacaa tcatgctgaa aggcaaaagt tgcgtcttac  34740
atggtggctg gcaagagaga gaatgagaac caagagaacg gggtttcccc ttataaaacc  34800
aacagatctc atgagactta ttcactacta tgagaacagt atgggggaaa ccacccctat  34860
gattcaatga tcacccaccg ggtccctccc acaacacgtg ggattatggg gagctgcaat  34920
tctagatgag atttgggtgg ggacacagcc aaaccatatc accaaggctg gagtgcagtg  34980
gtatgatcat ggctcattgc agcctccaac ttctgggttc aagcaatcct cccacctcag  35040
cctcctgatt agtggtgact acaggtgtgt gacaccacct ctggctggct tttaaatttt  35100
ttggagagat ggagtcttgc tattttgccc aggctggtct caaactcttg gtctcaaatg  35160
atcttcccat cttgacttcc caaagcactg agattacagg tgtgagccat tgcacctggc  35220
tggttctcat ttatttaagt attactgctg tcatggtttg ctttggtccc tgtgggttcc  35280
cccacccttt gaaacaagtg cctgacacat ggtagggttc acaataaata tttgtagaat  35340
aaataagagc tgagccttca aggggtccaa aatacttgca cggagttttt ctaggtgggc  35400
acgatgccac ccagctgcag gactatttca gggtgttcat tggctcctct ggttgatctt  35460
ttgatgcctg tataagaact cccacttctc caaatctggg ggccacatct ttagagttct  35520
cagctttctg tctctcagga atgaaggaga taatatcact gattggagcc agattgtctg  35580
gatgttgaat cccagctcct tgctggtgcc tttgagaagt gactttagcc ctccatgtgc  35640
cttatttctg cctctgtaaa cggagatcat catagcacct ctcatgtggg gctgtttgac  35700
gattcggtga ggtatgtgca aagagctttt tgcacttgca aaaagtgtct gggatatcat  35760
tgtgtgctgt aagaatgagc tgtaatgatt atcactgaga cttgttgttg ggattaaaag  35820
agatcaggtc tgtcagggcc tggtacacaa gaggtactag aaaaataatg ggaggtttag  35880
gtgctccttc ctccagatac actcgtaaat atgactgctg tgtcgtcatc tactttttag  35940
ggatatgaag aatctgctgt gtgaccttag atgaataaat ctctgattca ctctgggcct  36000
tggttttccc tgcctctgaa aggggtatga tgtttccttc ccttttgcct gggcgcaggt  36060
actgggtgct ttgtagttaa gggagtatca gctggtggct caagggtaga ttctaacagg  36120
```

-continued

```
aacttccaag ctggagaaat actaggctac acctcagaga ggggaggtgg gtaagggagg  36180
cccctgctgg tgtgagcagg aggtgggtga gggaggcccc tgctggtgtg agctcgatcc  36240
tttatccctg agcttcagac tctcttaagc cttcccacat gagaaactga catccagatg  36300
gaggtgggga ccctgcaatg taaagccagg tcacctgtcc acagaggtgt gtctgataac  36360
cagggcatga taggttagag agtgtggtgg ctaaaagcac cagcccttgg atcacctgag  36420
gtcaggagtt caagacctgc ctggccaaca tggtgaaact ccatctctac taaacataca  36480
aaaattagct tggtgtggtg gtgggcacct gtaatcccag ctacttggga ggccgaagca  36540
ggagaatcac ttgaacccag gaggcagagg ttgcagtgag ctgagattgc gccatttcac  36600
tccagcctgg gtgacaaaag cgaaactctg tctcaaaaaa agcaccagcc ttagactcag  36660
agagaccagg atttgagctt gggggacctc agcttcctct ctgtgtgacc tcaggtaagc  36720
cacttatact ctttgggcct cagtttcctc atttgtaaaa ttgaggccgt gattgaacct  36780
ccttcaagag ctgttgtgag tgctataggg gatactatct taaagcactt aatgcagtgc  36840
ctggcacatg gtagttctgt agaagtgctt gctattttaa ttcacgtgca caggtcctgc  36900
ctgtgggtga gggctcagta gatggaacag cgatggttga tatagttggg attgtgagga  36960
ttattatgac aggggctaat ttgaatgggc ctgtgttgtc tgccctcccc actgccagcc  37020
tgatttccct ctgcctggct ttgcagctcc tcccattggc tgctggggtg taccccttgc  37080
atgcggatga gaaacgagtc aatgaagtcc cgtggggaat tgggatccag cgtgcactgg  37140
ttgtgctcca ctttcttggc aatgaagtcc tccagccctt gcagctcctt aaaggcctgt  37200
tgctgtggtc ctggcaggtg tttcatcacc gaagagaaca tctcatagag ctggggttgc  37260
agagagagga tgggaaggga aggaccgctg tcaggaggca ggaactgatg ggaatgggac  37320
ctgtgtcaga gcaagaaagg cactgggtta aaggcaccta cctgcccagg tgtttaggta  37380
tttcagtggg gctggatggg aacatatatg taagtcttca tgagggttaa gtgagaaggc  37440
tactgtccag aaatttaggt aacatggact gaggcacaca tccaggtttc aatgaaggtg  37500
gattggagcg cacagctagg tgttcagaca ttcaaggcag gatgtgttgg aaaacacctg  37560
ttcaactgtt tagctactca gacggggctg gtatgagggg agtgtcacct gtctaggtat  37620
gtaggcattc aggtgggcct ggttgaagac aactaccgag atacttattg ggtctggatt  37680
gggggctttt gttcagatgt tcaggtatta aagtggggct ggtgaagatg ttgaagagga  37740
ggggatacct gttgaggtgt ttacctatcc aagtgggatg cactgggggc acctctgtaa  37800
ggtgtgtgat tggaaagggt tggggaacac ttatttgggt gtctggggaa taatctgtct  37860
agatatttat gtgtttaggg tattggttag ggcacctgtc catgttttca ggtatttaag  37920
tgggtgaagt agagggcgct tggccagata ttccagtggg ctaatctggg acatttgtgt  37980
agatgtgaaa tgattatgat gggctggatt ttgcagcacc aggtgttcag gtatgcagga  38040
ggcgggttga ggcagtcact tgtccaggtg ttaaaatatt cagaagaact gggtagggag  38100
catctgttag aaattatggt aagttgggga tgggaacatg tgcccaggtg agagagctga  38160
gctgagggta tgcatcctgc cttcaggctc tgttttgggg atcatctgtt gagctatcca  38220
ggtgtccttg gagactgggt attgggcacc catcctgggt tctggtgcaa ctttccggtt  38280
gtccaatatt gggggctgat tttgagggga cactgtctgg aggggggtgg gagtttgggg  38340
cacctgtccc catgtagggg agcagttggc aggttgtggt aggggcgtga cagccaggct  38400
gcagccggtt acctgccccg tggagggtgc cgtgaactgg aagctttcca gcatcatgca  38460
cagcagtgac aggaactttt gtcctcatag tcaaagcggt ccccaaagac aatggagctg  38520
```

-continued

```
atgacattgg aggtggtacg gcttaggaag aaggtgggat agatgctgga gcttgcgggt  38580
gtggcggtgt attgggggag aagggggttg ggaagagagt caactcagag ctctgatgct  38640
agtctgagaa ttccaggagg cactgccctg atgagccaca ttcccagcgc cagactacag  38700
ggctgggagc gcgggcgcct ttccccacca aggcccggtc cccagacaga acgcgcgcgg  38760
gttcctcgcc ctgggcgttt tccttctccc gcctccacac tcggggtgtt ctgctcaccg  38820
cgcgtgccct agacggcctt gatgaggaag cccgccttct cctggatacc tccttgatgc  38880
cgcgcttgcc caccccgaag tcccgcaggg tggcgatgga gaagcgcctg agcggcttgg  38940
tgcgctccca ggtgcggcag gtcactcctg ggagaggaac gcaggggtgg ggagaggtca  39000
ggccgtggga acaggcacag aagcctcgcg caggagaact gcaaactcag tcagagaaac  39060
acagagagaa acagagaccg aacaggaaca agaggatcag aaaagagaca ggccagacag  39120
acagatgcac agcagaacag agggagacgg gacactccat ggagcatagg gagggaagga  39180
gggagagaaa aagacagaga tgggagaaga tgatggaagg gggggaagtg aggtatgggg  39240
agatctgcga ggagaaaata aaaatggtga aagagtcttt tttgtttgta tgtttgttta  39300
tttgtttttg agacggattc tcgctctgtc gcccaggctg aagtgcattg tcgccatctt  39360
ggccgctcgc tgcaacctcc accttccagg ttcaagcgta aaaatggtga aagactccta  39420
agctgagctg gtgaagacag aaaactacgg aaagagaaac agagacggtc gggaaggagg  39480
agagactgtt atcaggagag gaggctggag atgtggaagt aggaataccg cgaaatccta  39540
agacagagga agaagaagga gaggtcagtg gacagaggag aaactcagag aagcacagaa  39600
gctgagaagg acaaaaagac aaatgaagac agagaaccag ggttggaaaa cagaaaccca  39660
ggattgtcct cagagatggg gaaagaggag actccagtga gagaggcagg gagaaatctg  39720
gacagggaca gggacaggga tgctggagac aggcaagagg gagaggccgc aatgaaggga  39780
gctggggagc gaaggccaga caggggctc tgccgcagcc ttcagtgggc aggagagtca  39840
gggagaaggc tggggacacg gaggccatcg agtcggcctg gccaccttcc ccctcttggg  39900
caccccctca ccatagcctt tgaagagcca gtcgaaggtg gcctgctcgc ctcgcccgct  39960
gaactcctca gcctggtcca ccagagcctc cttgacggca tcatgtccgc acagcaccac  40020
gacccgccgg ggccccaggt gaatggtgaa cacggggcca tagcgctcac tgatctgatg  40080
gaggcaggtg ggagtggtta gagggagcag cccccactct gaatgggcgc agcaccgaga  40140
tatcatgtac tgggatgttt tgcccccagg ttctcacagt cagggagctg gacatcccaa  40200
gatcctgtct ttccagccta ggaccctgat gctgaaactc caaaactccc tttcctaaga  40260
ctctggtcca cactggtcaa tcccctgcca caaagcctca gccaactggg cagccccac  40320
cccgtgccac ccatctccct gccttgggac accttcatga tggagtcaca tatgtgctct  40380
gtgttcagct gcaggtagtt tccaataaag agcaatgggg tgggtcccaa aggcagcttc  40440
cccctgctct tcctctgctg ccagactgac atcaagacca tcacagtcag gctggccagc  40500
aaggccacca gaagcagccc tgaggccagc atggtggcag tggaatgata gatggtgacg  40560
gctggggtgg tttgccttta tactgcctga aaaaaagggg tggactttgg ctggttataa  40620
aatcacctca tttcacctcc caactacatc ctctccgtga accccaccta gctttggaca  40680
caaccagcaa aggaggagga gggggacccc agggaagctg aacagagagg gtacctcccg  40740
actaaatctg tggtacctca ggaggggtgc cccagggctg tggatttagg agcgggcaac  40800
agataagctg tagaacaaag gagttgggaa tatttgcata ggggagcact tgggctttgg  40860
```

-continued

```
atttgggatc tgggagtgag aatgcacccc aaaattgtgg atttgggggt tccgaggaga  40920
agaatgcaaa ggtctgggtt ttattagggt gagatggaag tgtggctgtg catctggggg  40980
tcttctgttg tggaggatgc agggttaagg gtctcaggag gggggattcc aggcatatgg  41040
acttgagagt cttggggcta ggaagaccca gggctgtggg tgtggagttt ctgggaggag  41100
gagtgtgtag caagcccagt aggtcgtccc agaaagccca gcagcccagc actgggccca  41160
ggggctgact tgattttgct tttgcccaga gctgtctctt gatgcccgga atcctcactg  41220
gaacctcaga gtgaggccag gatgggtgcc atggaaactc cactgaccat ctctggttgg  41280
caaaggggtg gaagaccaga gccatatttc aagggaaatt tccacacacc tggagaagag  41340
taccttgtgt tatcagttgg cagagggatt ggccaggtct ggagaaatag taacaacaac  41400
ccccaaatgg tggaaaaagc tcaagtgtcc caagggttgt aatttacaaa gacctccact  41460
ggtttccaac ccagatcctt agggaaaccc actagattga ttgtatcatc cctattaata  41520
ttatgattgt tgtttatctt tctcatttta tataagggtc tacagaggac agaaaacaga  41580
cagtaggcag gggacatgca tgagtggccc tgaactccca tctctcctgc tctgagtact  41640
tagttcccct ttctggattt ggttttccca ccagtagaaa gggagtattt aggaaaagat  41700
catatttgag ggtgagttaa gtctccttta agggcgattc ctgctttgtc aggggctact  41760
actattagca ggcagaggga acaatcgcag aagagattgg ggtaaactcc agtgttaggc  41820
acagaggtag atcctggggt gggtgtgagt ggagaaggga tgagtagccc tcctgtcctt  41880
ccctcaggga aattcttcct tagtaaacgg ggcagttacc ctttggtgag catggtcgta  41940
tatgggaaga ttaagtctag gtgtgtatga tctggtcgaa tctttgtaac agtgaggttt  42000
gttcatcatg atcatcctca ttttgaagat gagcagatct agactccata aatcctcttg  42060
agtgaggtca cacagggaat aagtgaggga gctgggatgt gaactttctt ctcatccccc  42120
gtcattgact ggcctagatc accctgggag tcaagtgcag gccaggctta gcaggaggtg  42180
agtgctgaga ctggcatcag cagtggacac actgatgaca ttggcgggtt ctgatatcag  42240
catcaggtgt gttcagggag ggaaaggcat cgtgttggct ttgggactgc ccccaggtgt  42300
atgcgaggat gggaaacaag ttggtactga acttgatacc aggagaatat tgaagtcatg  42360
tttggtgcca agagggctct gtgtgttgtt tcaggtttca ttgagggcat aagtgtgtcc  42420
tgcttcagga gggcgtaaga atggcaccat atagggtctg aggttggtcc cagtgggctg  42480
tgacatgagc atgaggcagg tgctgatatt ggtcctatgt gggtctgaga tgagcctcag  42540
ccagatc                                                            42547
```

<210> SEQ ID NO 13
<211> LENGTH: 1690
<212> TYPE: DNA
<213> ORGANISM: Mouse

<400> SEQUENCE: 13

```
gaagcattga ggaggatcac acacacagtt gtagggagaa cacagagaag taaattgctg     60
acaaacaagc agggatggac ctggtttcag ctctctcact ggaaacctgg gtgctcctag    120
caatcagctt ggtgctcctc taccgatatg ggactcgtaa acatgaactt tttaagaaac    180
agggaattcc tgggcccaaa cctctgccat ttttaggcac tgtgctgaat tattacaagg    240
gtttatggaa attcgacatg gagtgctata aaaagtatgg aaaaacatgg gggttgtttg    300
atggtcaaac gcctctcctt gctgtcacag acccagagac gattaagaat gtgctagtga    360
aggaatgttt ttctgtcttc acaaaccggc gggattttgg cccagtgggg ataatgagta    420
```

-continued

```
aagctatctc aatatctaag gatgatgaat ggaagagata tagagctttg ctgtccccca    480
cattcaccag tggaaaactc aaggagatgt tccctgtcat tgaacagtat ggagacattt    540
tggtaaagta cttgaggcag aaggcaaaga aaggcaagcc tgttactatg aaagatgtgt    600
taggtgctta cagcatggat gtgatcacca gcacatcatt tggagtgaac gtggattccc    660
tcaacaaccc agaggatcct tttgtggaga aagccaaaaa gcttttaaga tttgattttt    720
ttgatccttt gctcttctca gtagtacttt ttccattcct gacaccagta tatgagatgt    780
taaatatctg catgttccca aaggattcaa tagaattttt caaaaaattt gtggacagaa    840
tgaaggaaag ccgcctggat tctaagcaga agcaccgagt ggattttctt cagctgatga    900
tgaattctca taataattcc aaagacaaag tctctcataa agccctttct gacatggaga    960
tcacagccca gtcaattatc tttatttttg ctgggtatga aaccaccagt agcacacttt   1020
ccttcaccct gcattccttg gccactcacc ctgatatcca gaaaaaactg caggatgaga   1080
tcgatgaggc tctgcccaac aaggcacctc ccacgtatga tactgtgatg gagatggaat   1140
acctggatat ggtgcttaat gaaaccctca gattatatcc cattgctaat agacttgaga   1200
gagtctgtaa gaaagatgtt gaactcaatg gtgtgtatat ccccaaaggg tcaacagtga   1260
tgattccatc ttatgctctt caccatgacc cacagcactg gtcagagcct gaagaattcc   1320
aacctgaaag gttcagcaag gagaacaagg gcagcattga tccttatgta tatctgccct   1380
ttgggaatgg acccaggaac tgccttggca tgaggtttgc tctcatgaat atgaaacttg   1440
ctctcactaa aattatgcag aacttctcct tccagccttg taaggaaaca cagatacctc   1500
tgaaattaag cagacaagga cttcttcaac cagaaaaacc cattgttcta aaggttgtgc   1560
cacgggatgc agtcataact ggagcatgag tctccctcaa ggagttcttc tgagttcttc   1620
agaaaggcag tgtctaagaa catcggacat tttagtttca tcatgagtaa aattgagatg   1680
aataaggggc                                                          1690
```

```
<210> SEQ ID NO 14
<211> LENGTH: 2768
<212> TYPE: DNA
<213> ORGANISM: Human

<400> SEQUENCE: 14

cactgctgtg cagggcagga aagctccatg cacatagccc agcaaagagc aacacagagc     60
tgaaaggaag actcagagga gagagataag taaggaaagt agtgatggct ctcatcccag    120
acttggccat ggaaacctgg cttctcctgg ctgtcagcct ggtgctcctc tatctatatg    180
gaacccattc acatggactt tttaagaagc ttggaattcc agggcccaca cctctgcctt    240
ttttgggaaa tattttgtcc taccataagg gcttttgtat gtttgacatg gaatgtcata    300
aaaagtatgg aaaagtgtgg ggcttttatg atggtcaaca gcctgtgctg gctatcacag    360
atcctgacat gatcaaaaca gtgctagtga aagaatgtta ttctgtcttc acaaaccgga    420
ggccttttgg tccagtggga tttatgaaaa gtgccatctc tatagctgag gatgaagaat    480
ggaagagatt acgatcattg ctgtctccaa ccttcaccag tggaaaactc aaggagatgg    540
tccctatcat tgcccagtat ggagatgtgt tggtgagaaa tctgaggcgg gaagcagaga    600
caggcaagcc tgtcaccttg aaagacgtct ttggggccta cagcatggat gtgatcacta    660
gcacatcatt tggagtgaac atcgactctc tcaacaatcc acaagacccc tttgtggaaa    720
acaccaagaa gcttttaaga tttgattttt tggatccatt ctttctctca ataacagtct    780
```

-continued

```
ttccattcct catcccaatt cttgaagtat taaatatctg tgtgtttcca agagaagtta    840
caaatttttt aagaaaatct gtaaaaagga tgaaagaaag tcgcctcgaa gatacacaaa    900
agcaccgagt ggatttcctt cagctgatga ttgactctca gaattcaaaa gaaactgagt    960
cccacaaagc tctgtccgat ctggagctcg tggcccaatc aattatcttt atttttgctg   1020
gctatgaaac cacgagcagt gttctctcct tcattatgta tgaactggcc actcaccctg   1080
atgtccagca gaaactgcag gaggaaattg atgcagtttt acccaataag gcaccaccca   1140
cctatgatac tgtgctacag atggagtatc ttgacatggt ggtgaatgaa acgctcagat   1200
tattcccaat tgctatgaga cttgagaggg tctgcaaaaa agatgttgag atcaatggga   1260
tgttcattcc caaaggggtg gtggtgatga ttccaagcta tgctcttcac cgtgacccaa   1320
agtactggac agagcctgag aagttcctcc ctgaaagatt cagcaagaag aacaaggaca   1380
acatagatcc ttacatatac acaccctttg gaagtggacc cagaaactgc attggcatga   1440
ggtttgctct catgaacatg aaacttgctc taatcagagt ccttcagaac ttctccttca   1500
aaccttgtaa agaaacacag atccccctga aattaagctt aggaggactt cttcaaccag   1560
aaaaacccgt tgttctaaag gttgagtcaa gggatggcac cgtaagtgga gcctgaattt   1620
tcctaaggac ttctgctttg ctcttcaaga aatctgtgcc tgagaacacc agagacctca   1680
aattactttg tgaatagaac tctgaaatga agatgggctt catccaatgg actgcataaa   1740
taaccgggga ttctgtacat gcattgagct ctctcattgt ctgtgtagag tgttatactt   1800
gggaatataa aggaggtgac caaatcagtg tgaggaggta gatttggctc ctctgcttct   1860
cacgggacta tttccaccac ccccagttag caccattaac tcctcctgag ctctgataag   1920
agaatcaaca tttctcaata atttcctcca caaattatta atgaaaataa gaattatttt   1980
gatggctcta acaatgacat ttatatcaca tgttttctct ggagtattct ataagtttta   2040
tgttaaatca ataaagacca ctttacaaaa gtattatcag atgctttcct gcacattaag   2100
gagaaatcta tagaactgaa tgagaaccaa caagtaaata tttttggtca ttgtaatcac   2160
tgttggcgtg gggcctttgt cagaactaga atttgattat taacataggt gaaagttaat   2220
ccactgtgac tttgcccatt gtttagaaag aatattcata gtttaattat gccttttttg   2280
atcaggcaca gtggctcacg cctgtaatcc tagcagtttg ggaggctgag ccgggtggat   2340
cgcctgaggt caggagttca agacaagcct ggcctacatg gttgaaaccc catctctact   2400
aaaaatacac aaattagcta ggcatggtgg actcgcctgt aatctcacta cacaggaggc   2460
tgaggcagga gaatcacttg aacctgggag gcggatgttg aagtgagctg agattgcacc   2520
actgcactcc agtctgggtg agagtgagac tcagtcttaa aaaaatatgc ctttttgaag   2580
cacgtacatt ttgtaacaaa gaactgaagc tcttattata ttattagttt tgatttaatg   2640
ttttcagccc atctcctttc atatttctgg gagacagaaa acatgtttcc ctacacctct   2700
tgcattccat cctcaacacc caactgtctc gatgcaatga acacttaata aaaaacagtc   2760
gattggtc                                                            2768
```

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15

```
ccggaattca ggaaagacat gatactgtcg gcagaagcc                            39
```

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16
cgcggatccg gccgctgcag gcgcagaact ggtaggtatg g 41

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gatgtgctcc aggctaaagt t 21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
agaaacggaa tgttgtggag t 21

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
ccgcctctag agcggtttct taccaata 28

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
ccgccggatc cagccagagt aggcaaatct 30

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ggatgaatat gccctacatg 20

<210> SEQ ID NO 22
<211> LENGTH: 20
<212> TYPE: DNA
<213> ORGANISM: Artificial Sequence
<220> FEATURE:

-continued

<223> OTHER INFORMATION: Primer

<400> SEQUENCE: 22

```
tgatgggcag caggtctcat                                                20
```

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23

```
acagaaacta tgtgagcctg                                                20
```

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24

```
atgggacggt tcacatgttc                                                20
```

<210> SEQ ID NO 25
<211> LENGTH: 1450
<212> TYPE: DNA
<213> ORGANISM: Human

<400> SEQUENCE: 25

```
gtgagcttgc tccttaagtt acaggaactc tccttataat agacacttca ttttcctagt     60
ccatccctca tgaaaaatga ctgaccactg ctgggcagca ggagggatga taatcctaac    120
tccaatcact ggcaactcct gagatcagag gaaaaccagc aacagcgtgg gagtttgggg    180
agaggcattc cataccagat tctgtggcct gcaggtgaca tgctgcctaa gagaagcagg    240
agtctgtgac agccacccca acacgtgacg tcatggccag tagggaagat gagctgagga    300
actgtgtggt atgtggggac caagccacag gctaccactt taatgcgctg acttgtgagg    360
gctgcaaggg tttcttcagg agaacagtca gcaaaagcat tggtcccacc tgcccctttg    420
ctggaagctg tgaagtcagc aagactcaga ggcgccactg cccagcctgc aggttgcaga    480
agtgcttaga tgctggcatg aggaaagaca tgatactgtc ggcagaagcc ctggcattgc    540
ggcgagcaaa gcaggcccag cggcgggcac agcaaacacc tgtgcaactg agtaaggagc    600
aagaagagct gatccggaca ctcctggggg cccacacccg ccacatgggc accatgtttg    660
aacagtttgt gcagtttagg cctccagctc atctgttcat ccatcaccag cccttgccca    720
ccctggcccc tgtgctgcct ctggtcacac acttcgcaga catcaacact ttcatggtac    780
tgcaagtcat caagtttact aaggacctgc ccgtcttccg ttccctgccc attgaagacc    840
agatctccct tctcaaggga gcagctgtgg aaatctgtca catcgtactc aataccactt    900
tctgtctcca aacacaaaac ttcctctgcg ggcctcttcg ctacacaatt gaagatggag    960
cccgtgtggg gttccaggta gagtttttgg agttgctctt tcacttccat ggaacactac   1020
gaaaactgca gctccaagag cctgagtatg tgctcttggc tgccatggcc ctcttctctc   1080
ctgaccgacc tggagttacc cagagagatg agattgatca gctgcaagag gagatggcac   1140
tgactctgca aagctacatc aagggccagc agcgaaggcc ccgggatcgg tttctgtatg   1200
cgaagttgct aggcctgctg gctgagctcc ggagcattaa tgaggcctac gggtaccaaa   1260
```

-continued

```
tccagcacat ccagggcctg tctgccatga tgccgctgct ccaggagatc tgcagctgag   1320

gccatgctca cttccttccc cagctcacct ggaacaccct ggatacactg gagtgggaaa   1380

atgctgggac caaagattgg gccgggttca aagggagccc agtggttgca atgaaagact   1440

aaagcaaaac                                                          1450
```

<210> SEQ ID NO 26
<211> LENGTH: 1350
<212> TYPE: DNA
<213> ORGANISM: Mouse

<400> SEQUENCE: 26

```
cttgttttcc aggcactgag gaccgcagtc cctaattcct ggcagttcct gagatctcaa     60

ggaaagcagg gtcagcgagg aggcctgggg agaggaggca tcctacaccc aatcttgtgg    120

cctgctgcct aagggaaaca ggagaccatg acagctatgc taacactaga aaccatggcc    180

agtgaagaag aatatgggcc gaggaactgt gtggtgtgtg gagaccgggc cacaggctat    240

catttccacg ccctgacttg tgagggctgc aagggcttct tcagacgaac agtcagcaaa    300

accattggtc ccatctgtcc gtttgctgga aggtgtgagg tcagcaaggc ccagagacgc    360

cactgtccag cctgcaggtt gcagaagtgt ctaaatgttg gcatgaggaa agacatgata    420

ctgtcagcag aagccctggc attgcggcga gccagacagg cacagcggcg ggcagagaaa    480

gcatctttgc aactgaatca gcagcagaaa gaactggtcc agatcctcct gggggcccac    540

actcgccatg tgggcccatt gtttgaccag tttgtgcagt tcaagcctcc agcctatctg    600

ttcatgcatc accggccttt ccagcctcgg ggccccgtgt tgcctctgct cacacacttt    660

gcagatatca acacgtttat ggtgcaacag atcatcaagt tcaccaagga tctgccgctc    720

ttccggtccc taaccatgga ggaccagatc tcccttctca agggagcggc tgtggaaata    780

ttgcatatct cactcaacac tacgttctgt cttcaaacag agaatttctt ctgtgggcct    840

ctttgctaca agatggagga cgcagtccat gcagggttcc agtacgagtt tttggagtcg    900

atcctccact tccataaaaa cctgaaagga ctgcatctcc aggagcctga gtatgtgctc    960

atggctgcca cggccctctt ctcccctgac agacccggag ttacccaaag agaagagata   1020

gatcagctac aagaggagat ggcgctgatt ctgaacaacc acattatgga acaacagtct   1080

cggctccaaa gtcggtttct gtatgcaaag ctgatgggcc tgctggctga cctccggagt   1140

ataaacaatg catactccta tgaacttcag cgcttggagg aactgtctgc tatgacgccg   1200

ctgctcgggg agatttgcag ttgaggccca ggcttgcatc ctttccccag acccccaggg   1260

atacactggc ctggaaaggg tacagcgctg gaccccacac gggaaccagc aggaaggagc   1320

ttgggagtgg caatgaaatg ctgaacagtc                                    1350
```

<210> SEQ ID NO 27
<211> LENGTH: 286
<212> TYPE: PRT
<213> ORGANISM: Mouse

<400> SEQUENCE: 27

```
Met Thr Ala Met Leu Thr Leu Glu Thr Met Ala Ser Glu Glu Glu Tyr
1               5                   10                  15

Gly Pro Arg Asn Cys Val Val Cys Gly Asp Arg Ala Thr Gly Tyr His
            20                  25                  30

Phe His Ala Leu Thr Cys Glu Gly Cys Lys Gly Phe Phe Arg Arg Thr
        35                  40                  45
```

-continued

```
Val Ser Lys Thr Ile Gly Pro Ile Cys Pro Phe Ala Gly Arg Cys Glu
    50                  55                  60

Val Ser Lys Ala Gln Arg Arg His Cys Pro Ala Cys Arg Leu Gln Lys
65                  70                  75                  80

Cys Leu Asn Val Gly Met Arg Lys Asp Met Ile Leu Ser Ala Glu Ala
                85                  90                  95

Leu Ala Leu Arg Arg Ala Arg Gln Ala Gln Arg Arg Ala Glu Lys Ala
            100                 105                 110

Ser Leu Gln Leu Asn Gln Gln Gln Lys Glu Leu Val Gln Ile Leu Leu
        115                 120                 125

Gly Ala His Thr Arg His Val Gly Pro Leu Phe Asp Gln Phe Val Gln
    130                 135                 140

Phe Lys Pro Pro Ala Tyr Leu Phe Met His His Arg Pro Phe Gln Pro
145                 150                 155                 160

Arg Gly Pro Val Leu Pro Leu Leu Thr His Phe Ala Asp Ile Asn Thr
                165                 170                 175

Phe Met Val Gln Gln Ile Ile Lys Phe Thr Lys Asp Leu Pro Leu Phe
            180                 185                 190

Arg Ser Leu Thr Met Glu Asp Gln Ile Ser Leu Leu Lys Gly Ala Ala
        195                 200                 205

Val Glu Ile Leu His Ile Ser Leu Asn Thr Thr Phe Cys Leu Gln Thr
    210                 215                 220

Glu Asn Phe Phe Cys Gly Pro Leu Cys Tyr Lys Met Glu Asp Ala Val
225                 230                 235                 240

His Ala Gly Phe Gln Tyr Glu Phe Leu Glu Ser Ile Leu His Phe His
                245                 250                 255

Lys Asn Leu Lys Gly Leu His Leu Gln Glu Pro Glu Tyr Val Leu Met
            260                 265                 270

Ala Ala Thr Ala Leu Phe Ser Pro Gly Phe Cys Met Gln Ser
        275                 280                 285
```